(12) United States Patent
Yang et al.

(10) Patent No.: US 11,666,604 B2
(45) Date of Patent: Jun. 6, 2023

(54) MULTILAYERED CELL SHEET OF CARDIAC STEM CELLS AND METHOD OF PREPARING THE SAME

(71) Applicants: INJE UNIVERSITY INDUSTRY-ACADEMIC COOPERATION FOUNDATION, Gimhae-si (KR); AJOU UNIVERSITY INDUSTRY-ACADEMIC COOPERATION FOUNDATION, Suwon-si (KR)

(72) Inventors: Young-Il Yang, Busan (KR); Ki-Dong Park, Seoul (KR); Won-Jin Lee, Busan (KR); Min-Young Choi, Gimhae-si (KR); Kyung-Min Park, Anyang-si (KR); Yun-Ki Lee, Seongnam-si (KR)

(73) Assignees: INJE UNIVERSITY INDUSTRY-ACADEMIC COOPERATION FOUNDATION, Gimhae-si (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 1233 days.

(21) Appl. No.: 15/779,073

(22) PCT Filed: Dec. 18, 2017

(86) PCT No.: PCT/KR2017/014952
§ 371 (c)(1),
(2) Date: May 24, 2018

(87) PCT Pub. No.: WO2018/117569
PCT Pub. Date: Jun. 28, 2018

(65) Prior Publication Data
US 2021/0196761 A1  Jul. 1, 2021

(30) Foreign Application Priority Data
Dec. 20, 2016 (KR) .................. 10-2016-0174541

(51) Int. Cl.
A61K 35/34 (2015.01)
C12N 5/0775 (2010.01)

(52) U.S. Cl.
CPC ............ *A61K 35/34* (2013.01); *C12N 5/0662* (2013.01); *C12N 2501/15* (2013.01); *C12N 2501/155* (2013.01); *C12N 2501/17* (2013.01); *C12N 2501/235* (2013.01); *C12N 2533/52* (2013.01); *C12N 2533/54* (2013.01); *C12N 2533/56* (2013.01)

(58) Field of Classification Search
CPC .................. A61K 35/34; C12N 5/0662; C12N 2501/15; C12N 2501/155; C12N 2501/17; C12N 2501/235; C12N 2533/52; C12N 2533/54; C12N 2533/56; C12N 2513/00
See application file for complete search history.

(56) References Cited

U.S. PATENT DOCUMENTS

| 2009/0053277 A1 | 2/2009 | Nagaya et al. |
| 2013/0295060 A1 | 11/2013 | Yang et al. |
| 2016/0121025 A1 | 5/2016 | Yamashita et al. |
| 2017/0247658 A1 | 8/2017 | Iseoka et al. |

FOREIGN PATENT DOCUMENTS

| KR | 10-2008-0100126 A | 11/2008 |
| KR | 10-2012-0063619 A | 6/2012 |
| KR | 10-2013-0124075 A | 11/2013 |
| KR | 10-2016-0005366 A | 1/2016 |
| WO | 2016-076368 A1 | 5/2016 |

OTHER PUBLICATIONS

Kim et al. Tissue engineered cardiac stem cell grafts for repairing heart with myocardial infarction. FASEB. 2010;24:Abstract (Year: 2010).*

Li TS, Cheng K, Malliaras K, Matsushita N, Sun B, Marbán L, Zhang Y, Marbán E. Expansion of human cardiac stem cells in physiological oxygen improves cell production efficiency and potency for myocardial repair. Cardiovasc Res. Jan. 1, 2011;89(1):157-65 (Year: 2011).*

Bax NA, van Marion MH, Shah B, Goumans MJ, Bouten CV, van der Schaft DW. Matrix production and remodeling capacity of cardiomyocyte progenitor cells during in vitro differentiation. J Mol Cell Cardiol. Oct. 2012;53(4):497-508. (Year: 2012).*

Yuan Ye K, Sullivan KE, Black LD. Encapsulation of cardiomyocytes in a fibrin hydrogel for cardiac tissue engineering. J Vis Exp. Sep. 19, 2011;(55):3251. (Year: 2011).*

Li TS, Cheng K, Malliaras K, Matsushita N, Sun B, Marbán L, Zhang Y, Marbán E. Expansion of human cardiac stem cells in physiological oxygen improves cell production efficiency and potency for myocardial repair. Cardiovasc Res. Jan. 1, 2011 ;89(1):157-65 Supplementary materials (Year: 2011).*

(Continued)

*Primary Examiner* — Taeyoon Kim
(74) *Attorney, Agent, or Firm* — Revolution IP, PLLC

(57) ABSTRACT

Disclosed are a multilayered cell sheet of cardiac stem cells (CSCs) and a method of manufacturing the same. In particular, the present disclosure provides a method of manufacturing a multilayered cell sheet according to a single step culture procedure by using, as a three-dimensional matrix, a biodegradable natural polymer hydrogel and embedding CSCs in the hydrogel. The multilayered cell sheet of the present disclosure does not require any special device for the manufacturing, is manageable with good physicomechanical property, increases a cell engraftment rate after transplantation based on sufficient accumulation of various growth and protective factors and extracellular matrix between cells, and is also self-assembled by the cell-mediated hydrogel compaction, making nutrients transfer easy. Therefore, the multilayered cell sheet of the CSCs is expected to be usefully applicable as a therapeutic agent for myocardium regeneration.

8 Claims, 20 Drawing Sheets

(56) References Cited

OTHER PUBLICATIONS

Bian et al. Engineered skeletal muscle tissue networks with controllable architecture. Biomaterials. Mar. 2009 ; 30(7): 1401-1412 (Year: 2009).*
International Search Report for PCT/KR2017/014952 dated Apr. 6, 2018 from Korean Intellectual Property Office.

* cited by examiner

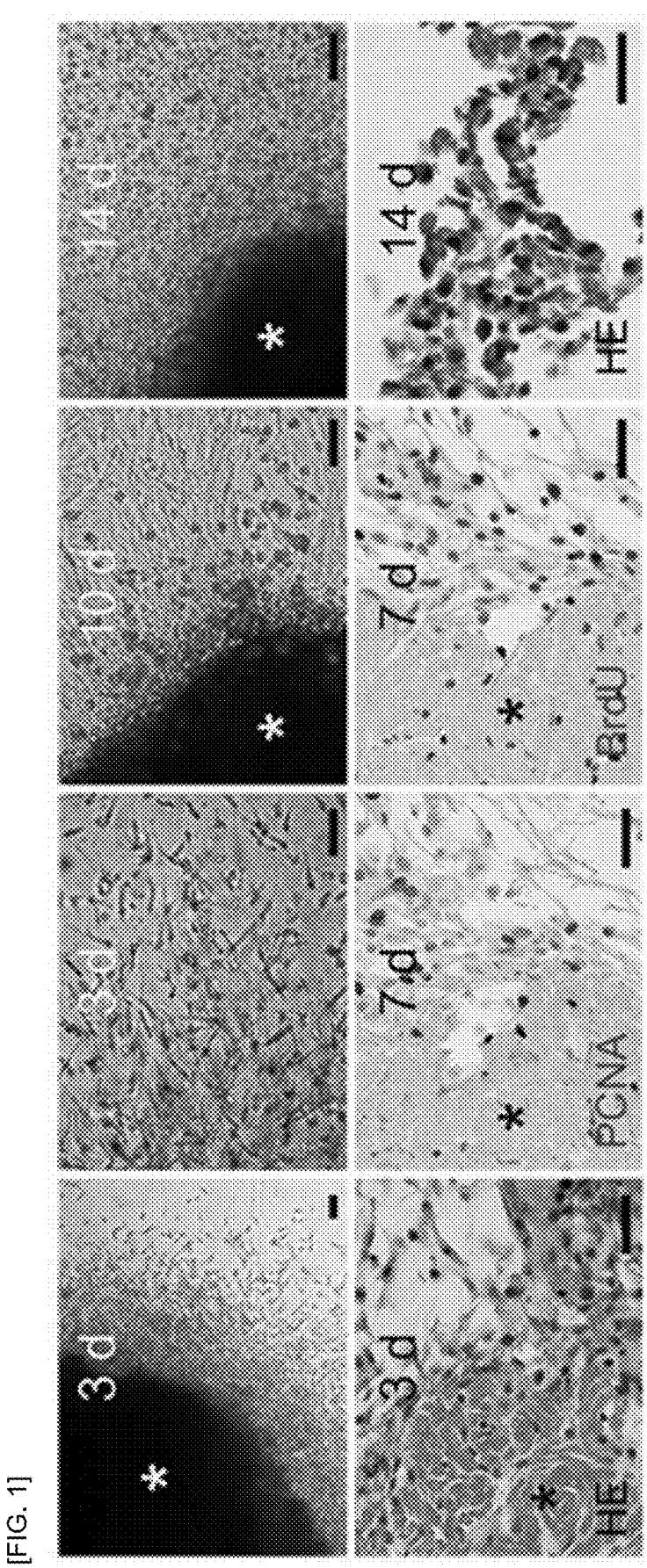
[FIG. 1]

[FIG. 2]
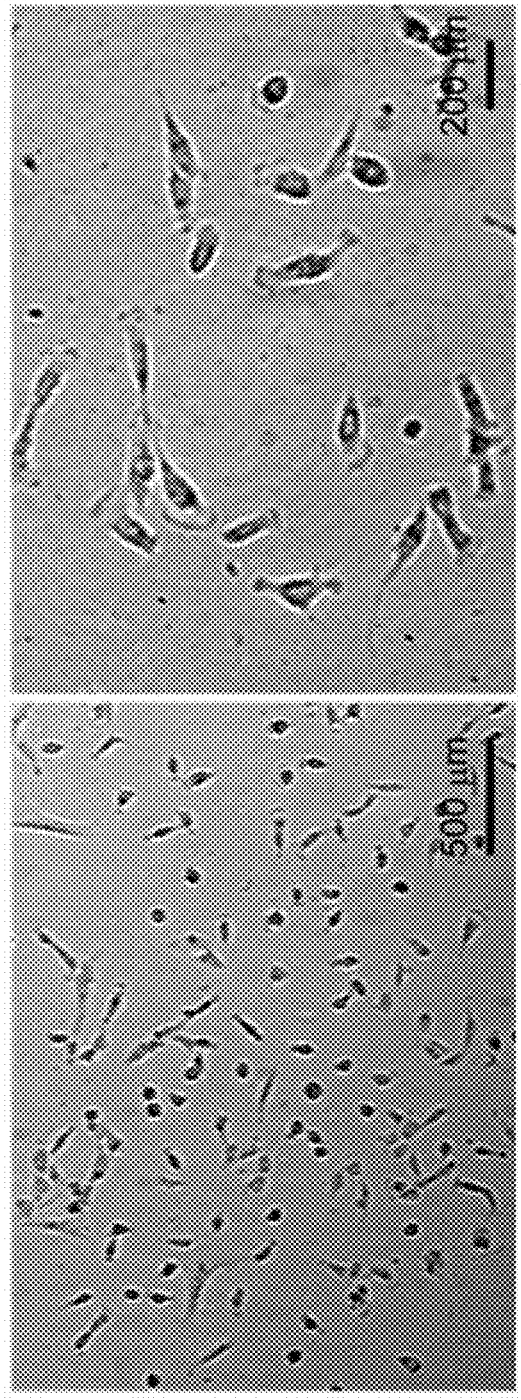
[FIG. 3]
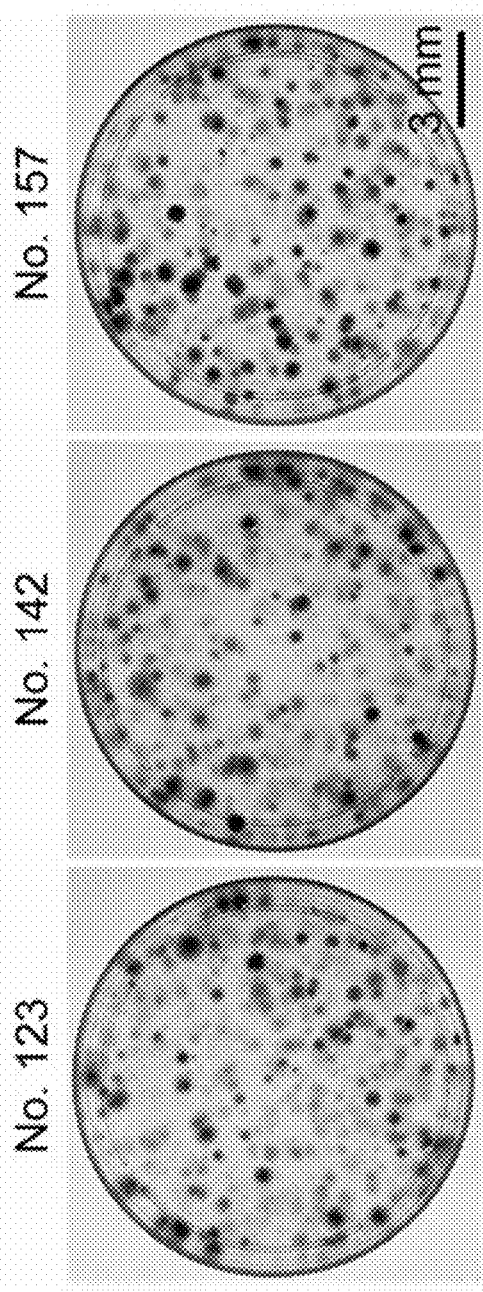

[FIG. 4]
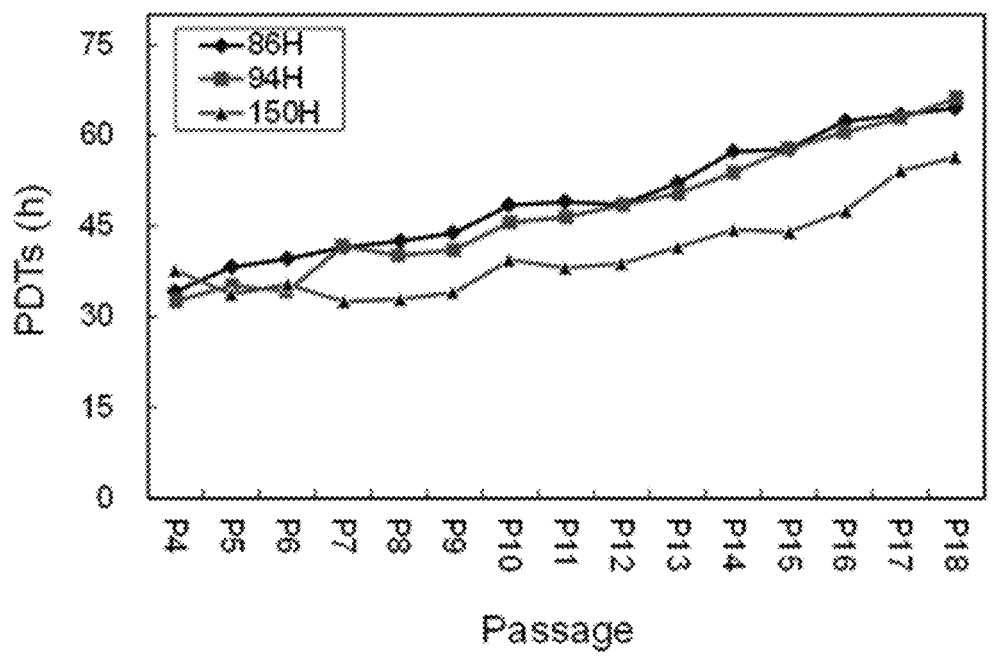
[FIG. 5]
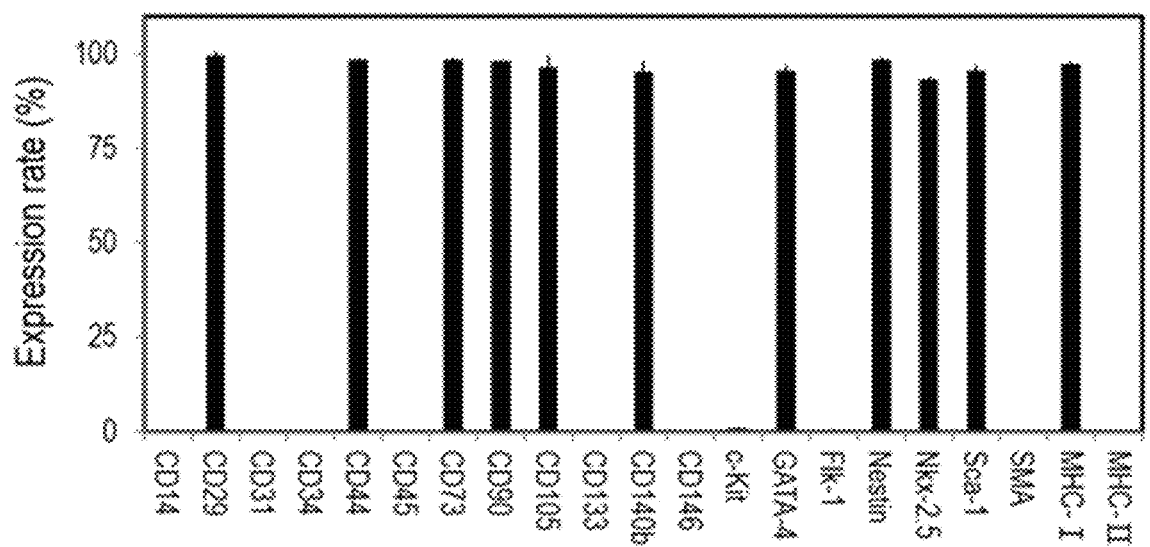

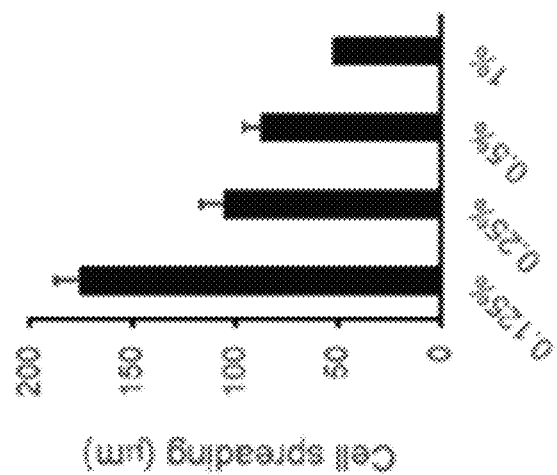
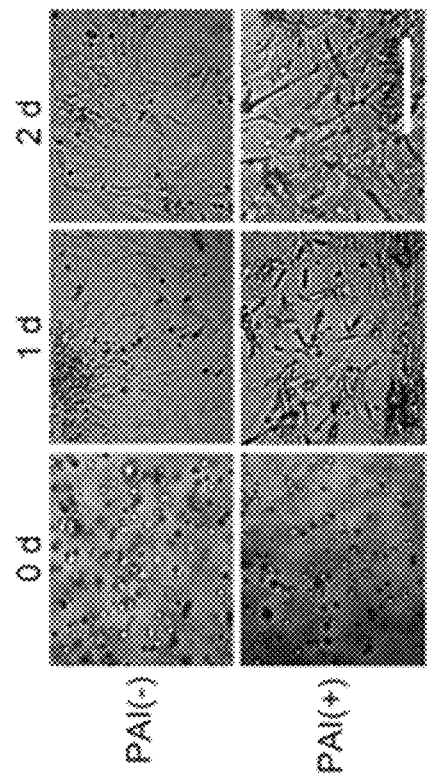
[FIG. 6]
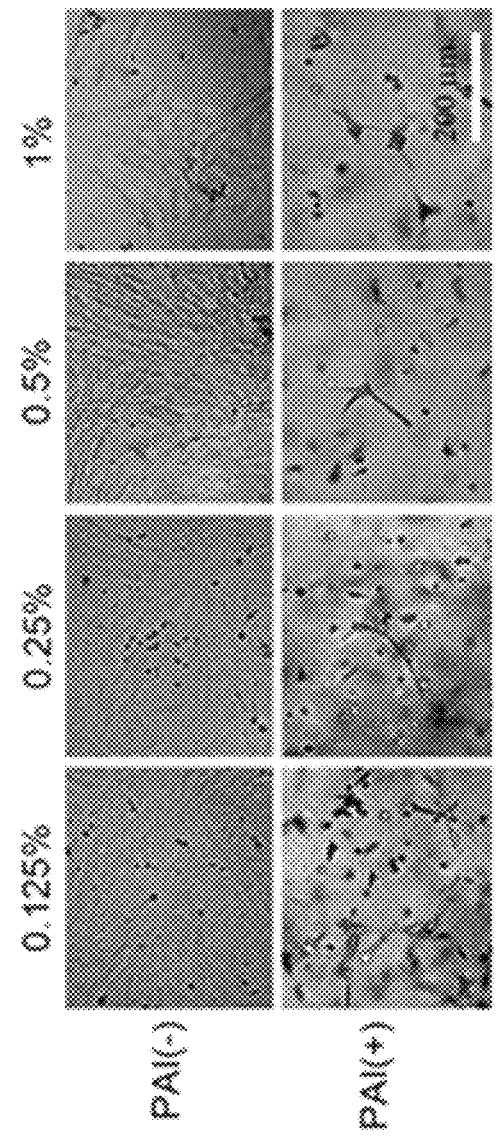
[FIG. 7]

[FIG. 8]
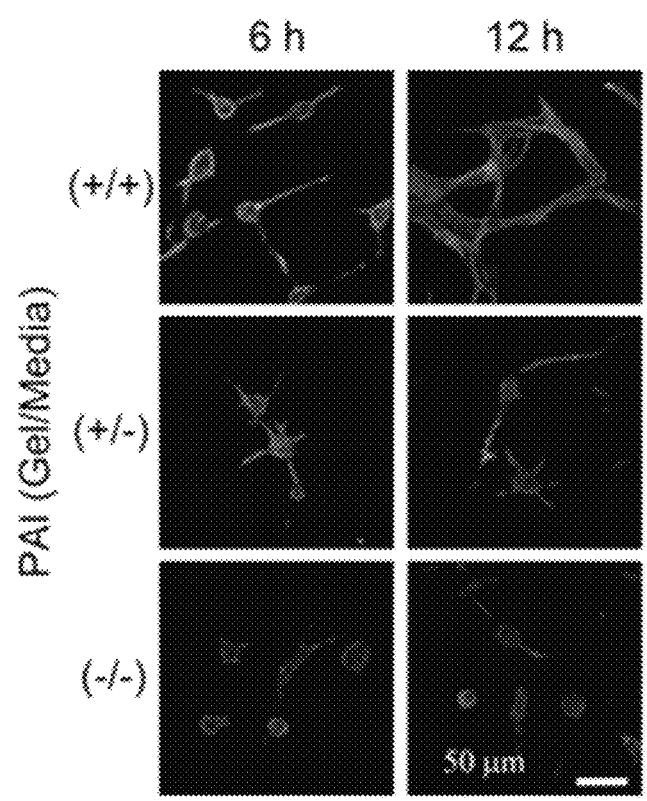

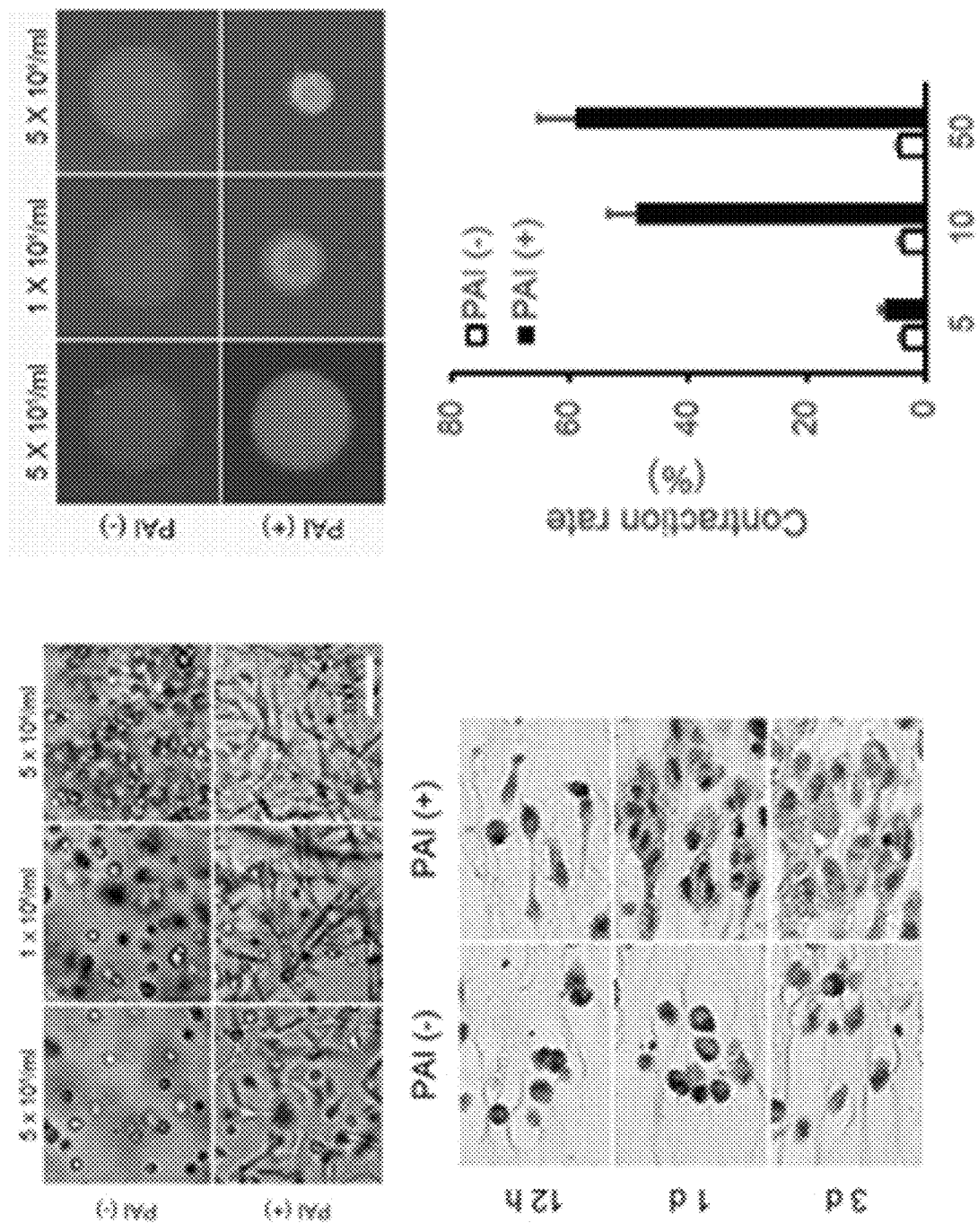
[FIG. 9]

[FIG. 10]
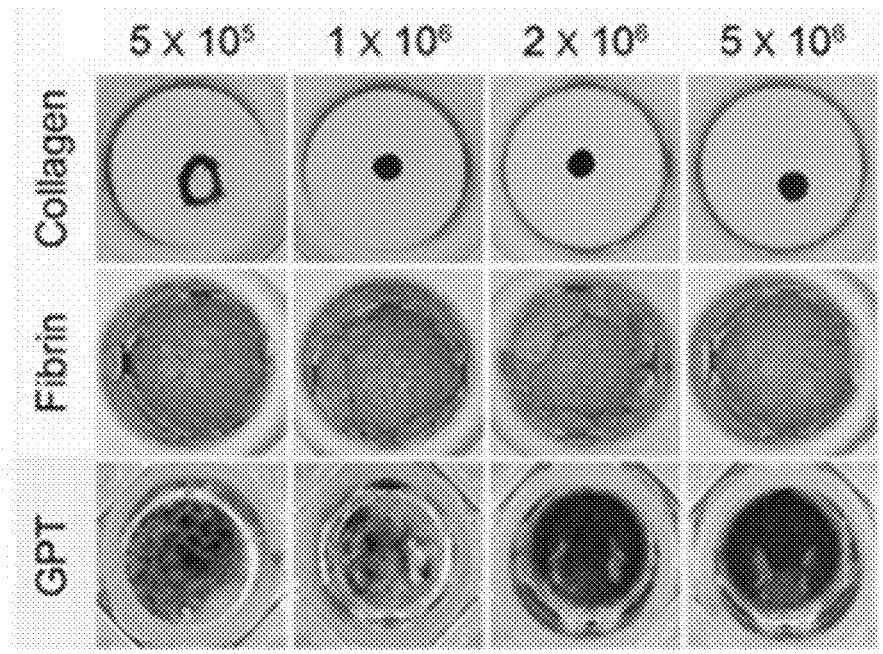

[FIG. 11]
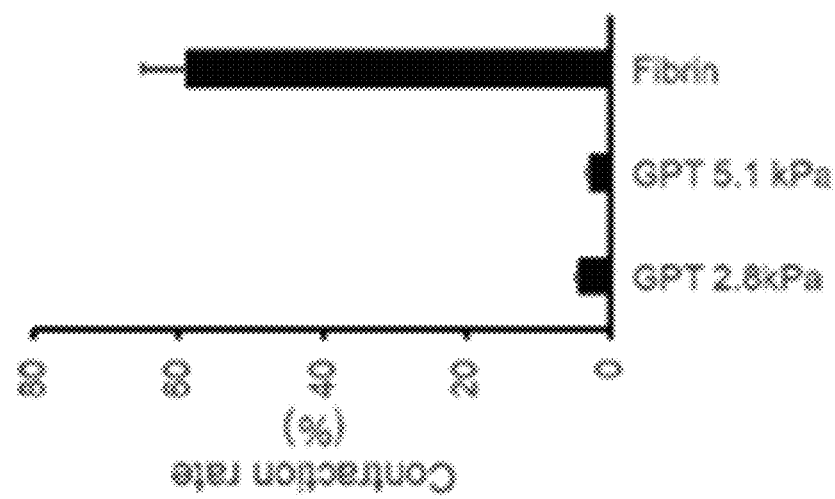
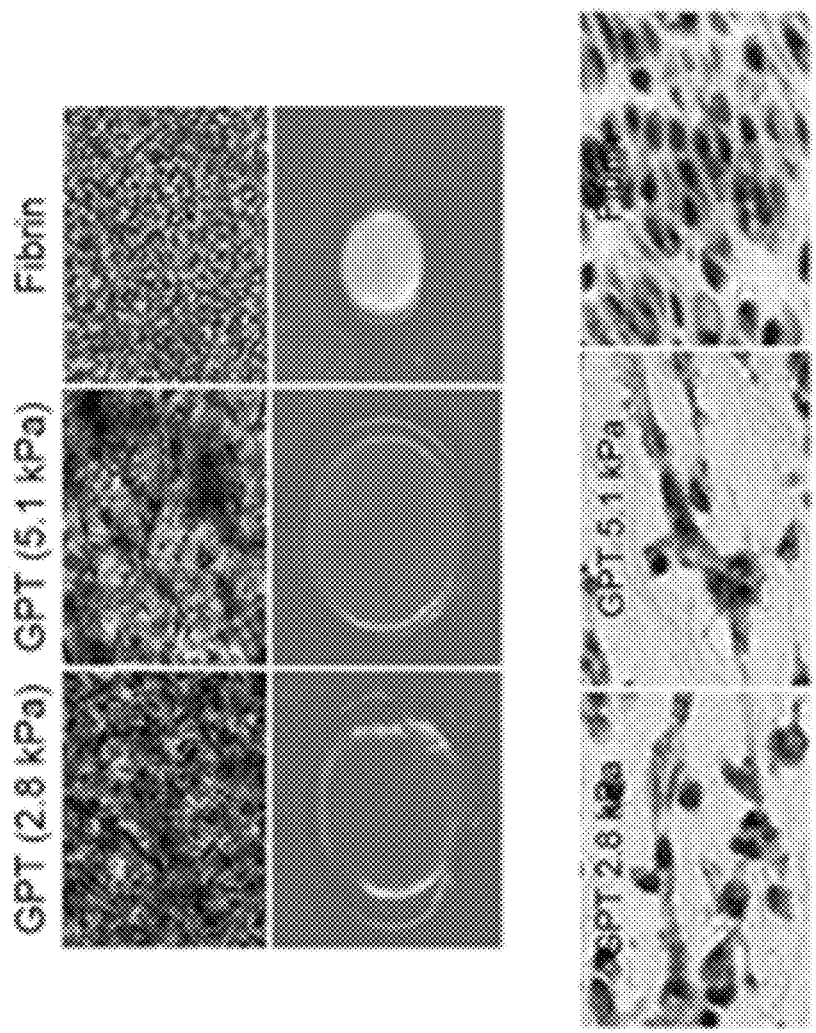

[FIG. 12]
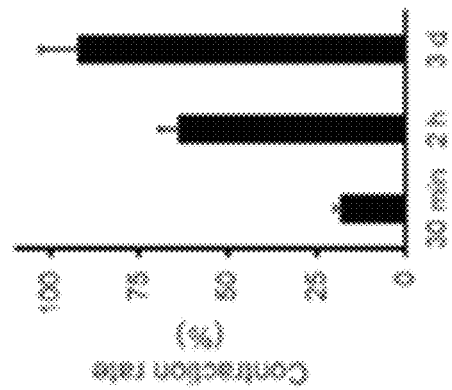
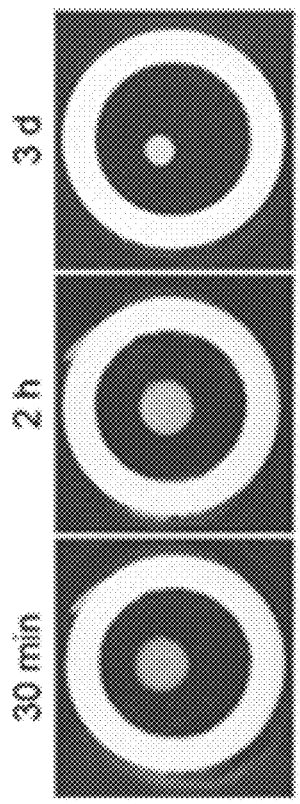

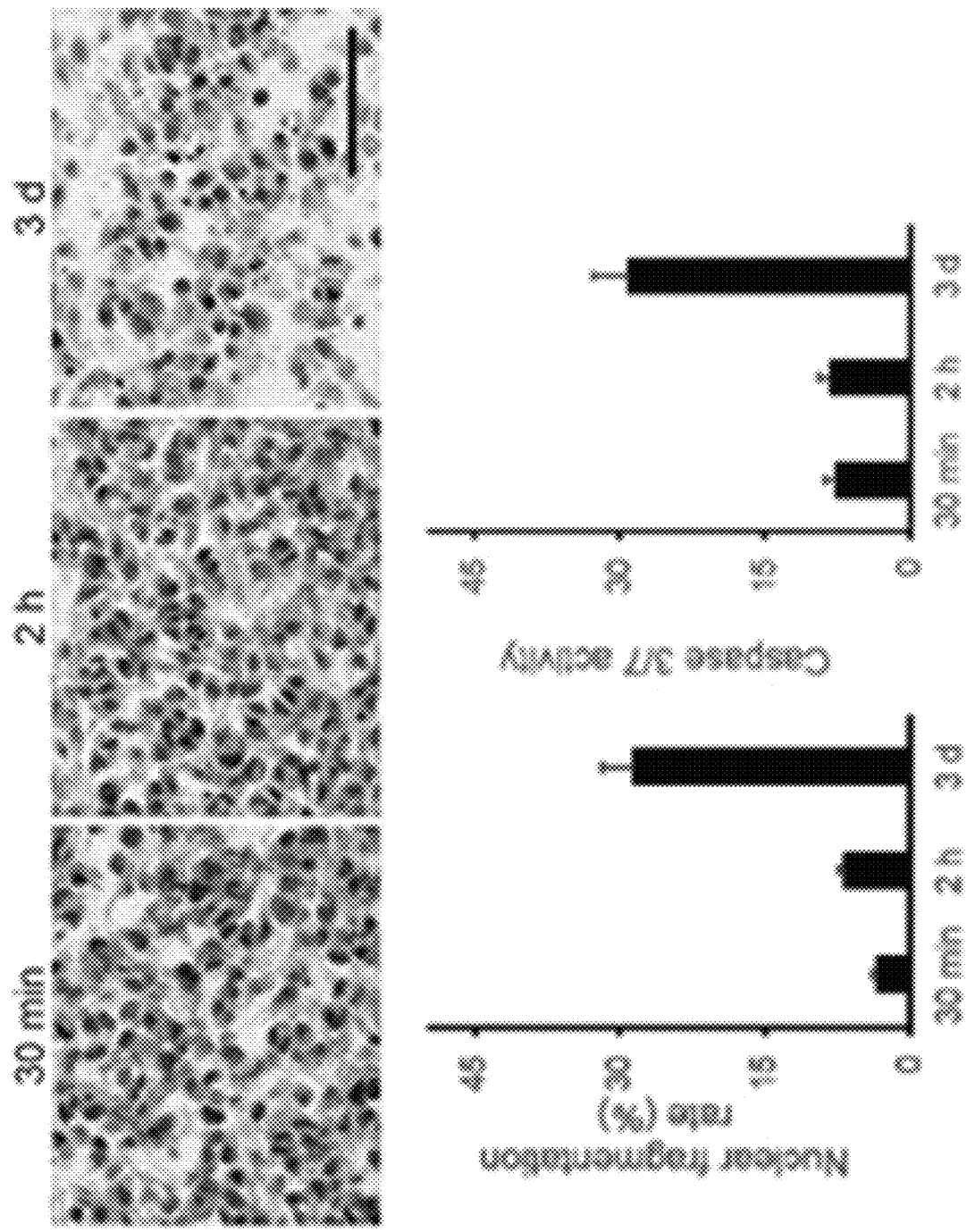
[FIG. 13]

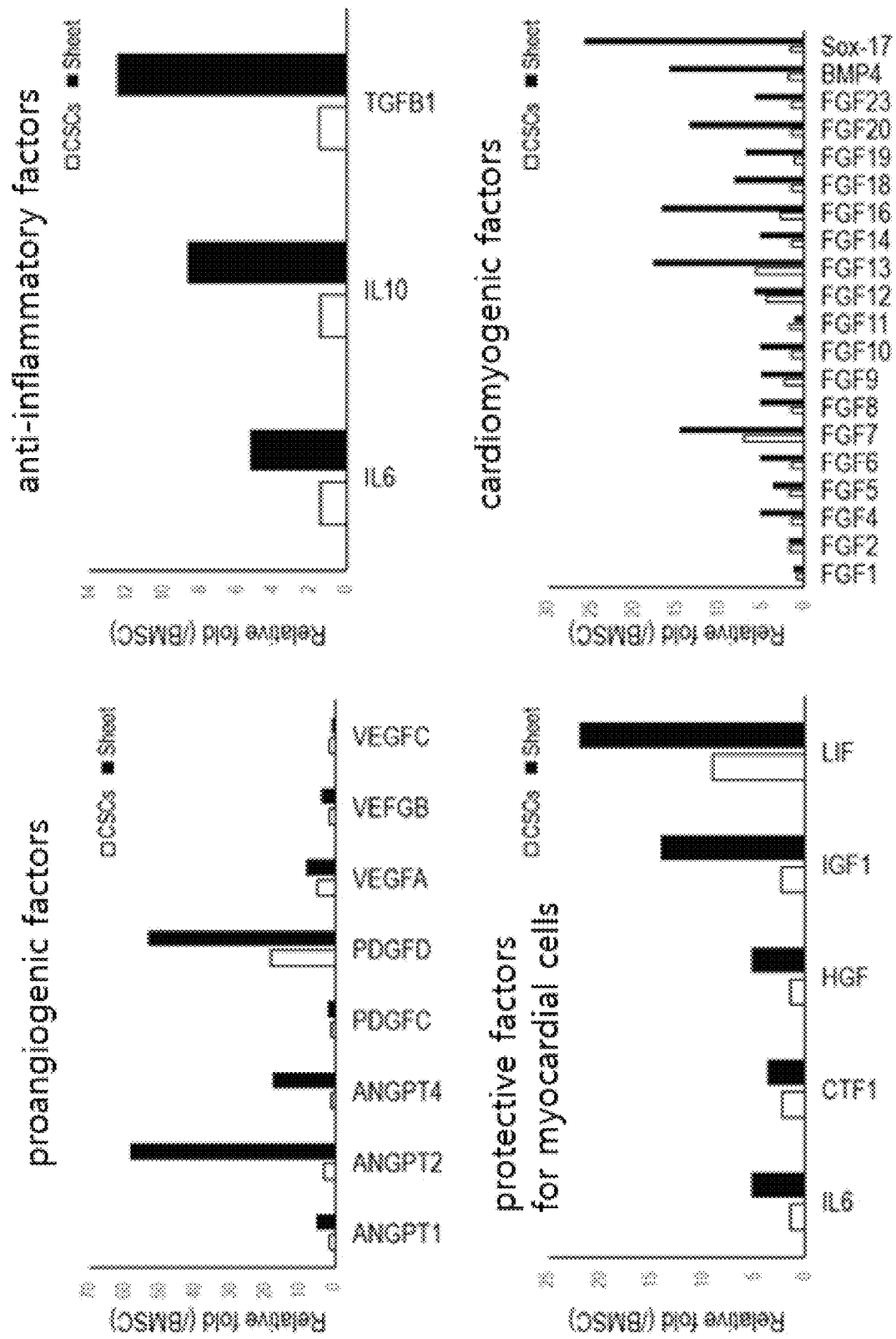
[FIG. 14]

[FIG. 15]
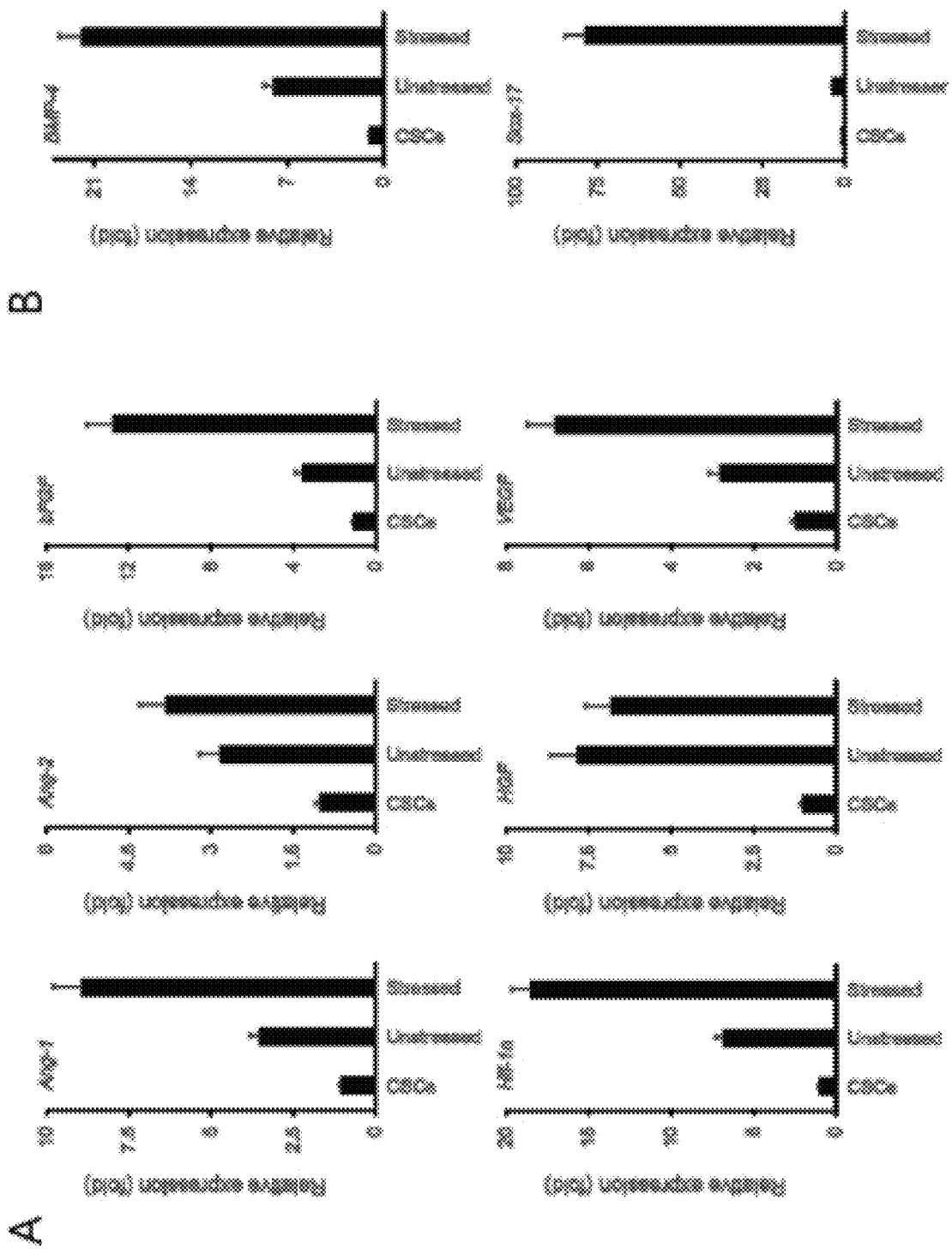

[FIG. 16]
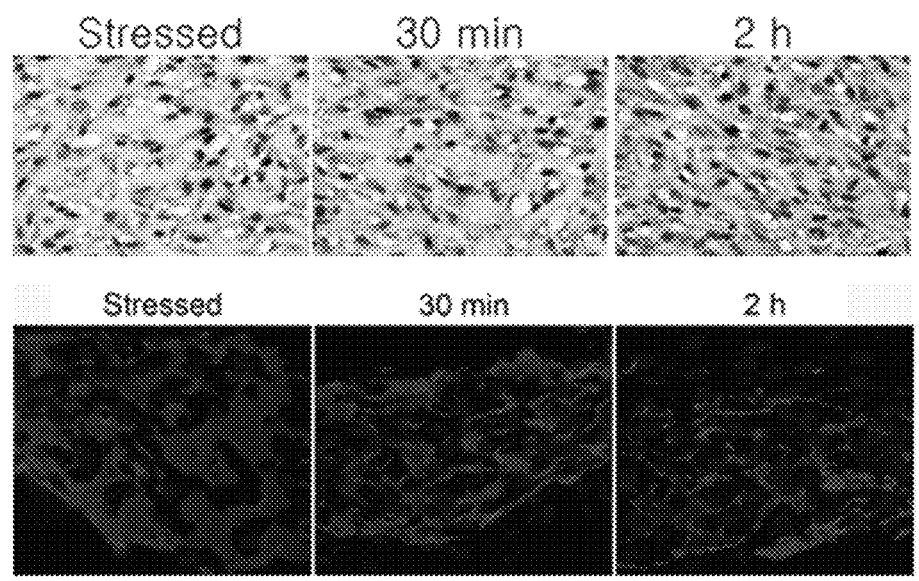

[FIG. 17]
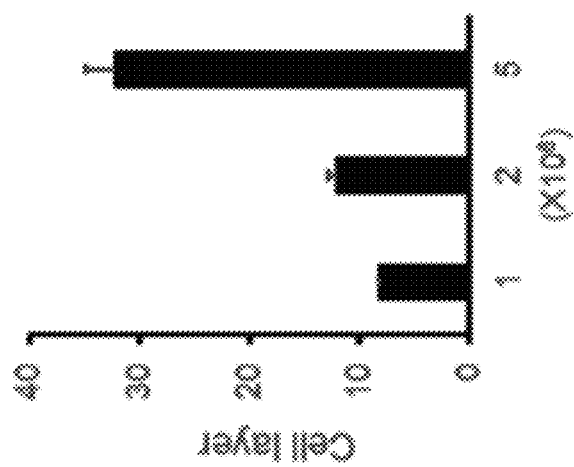
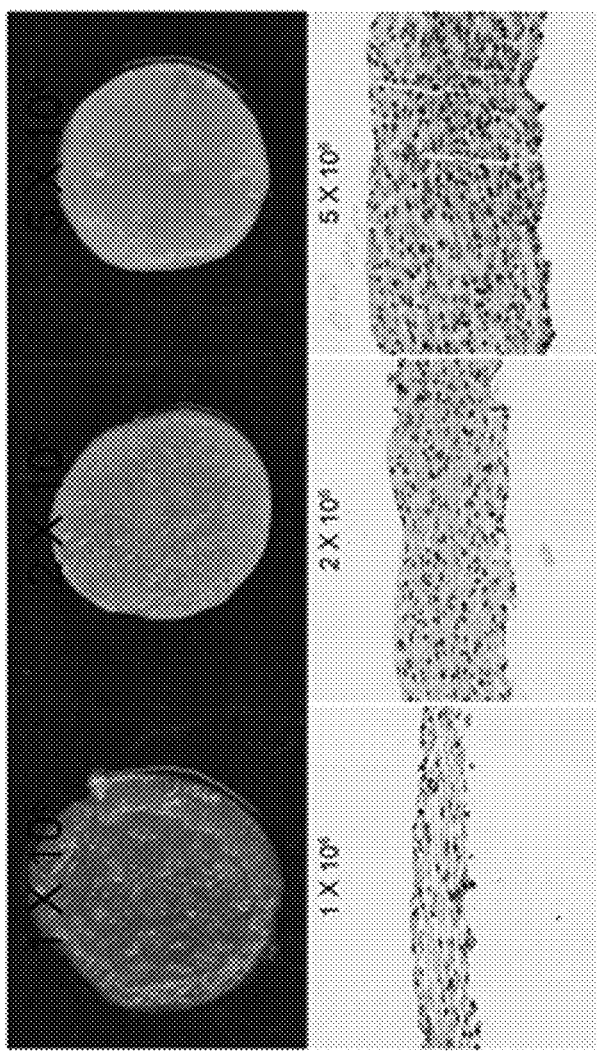
[FIG. 18]
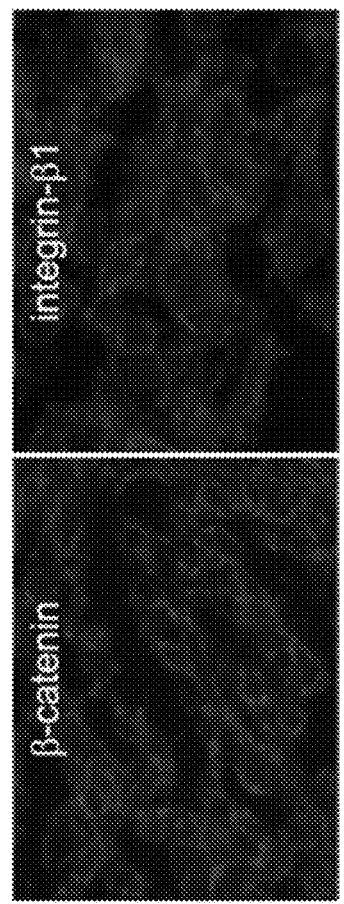

[FIG. 19]
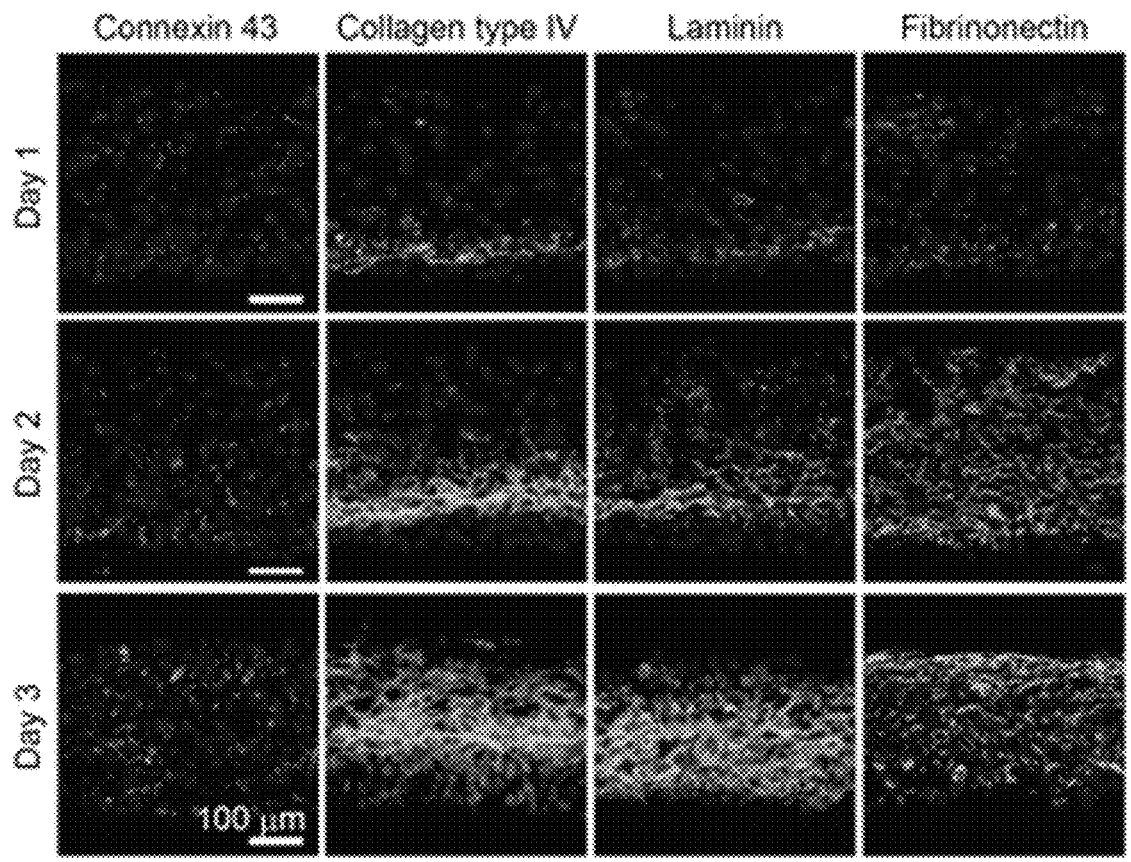
[FIG. 20]
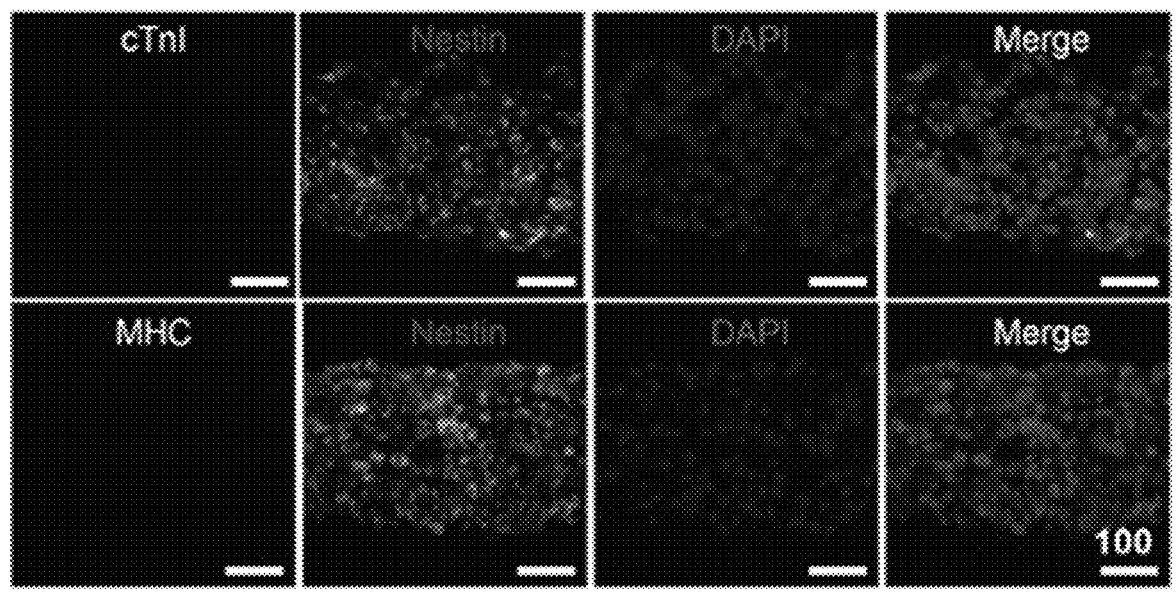

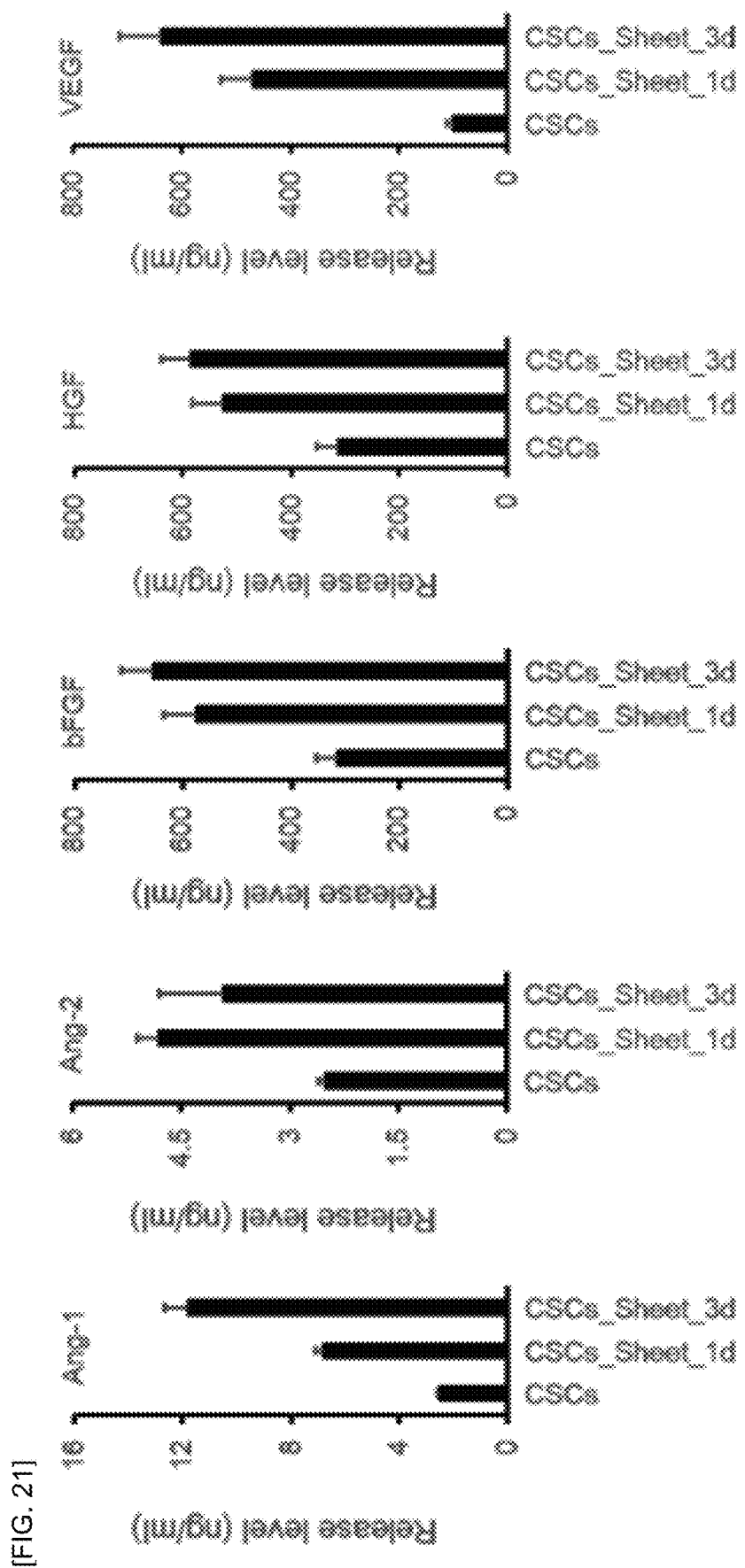
[FIG. 21]

[FIG. 22]
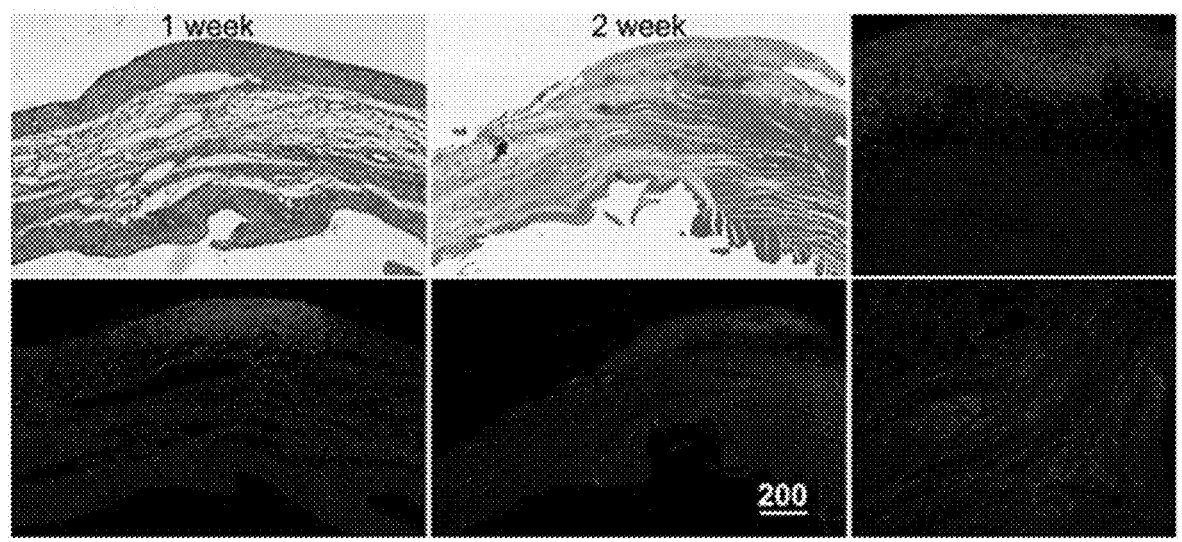

[FIG. 23]
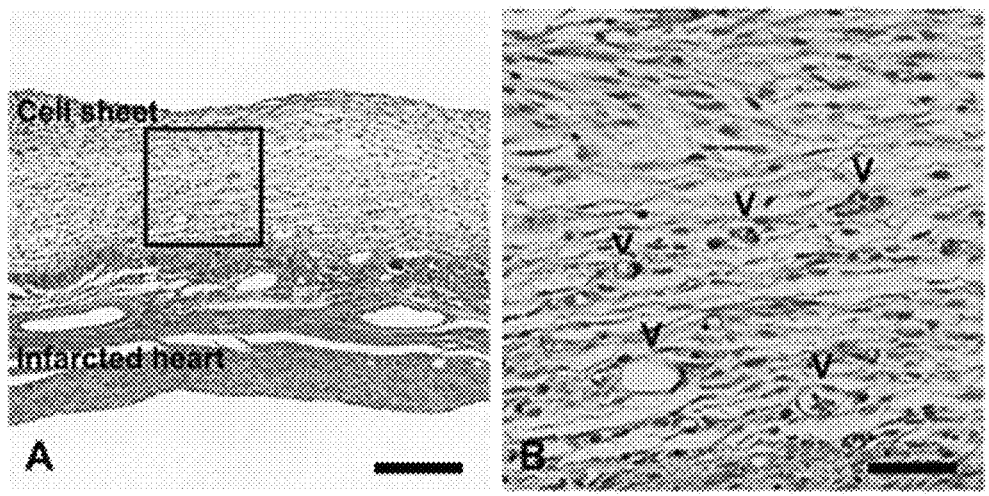
[FIG. 24]
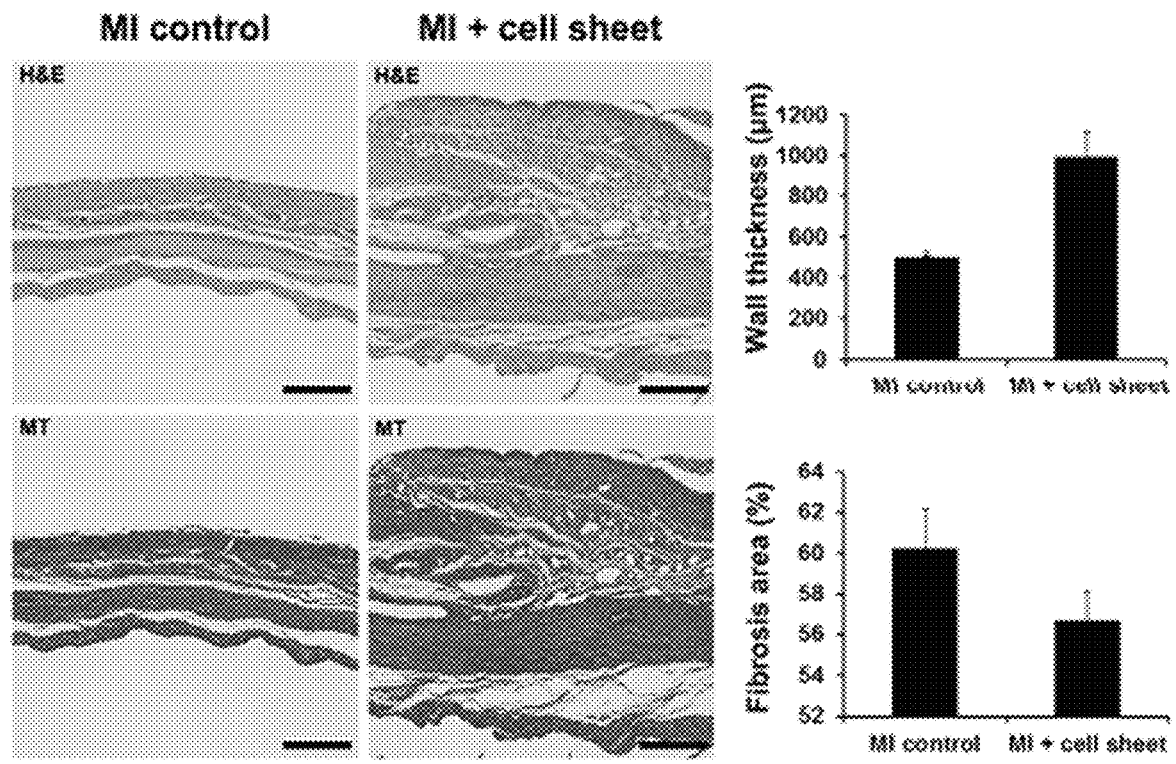

[FIG. 25]
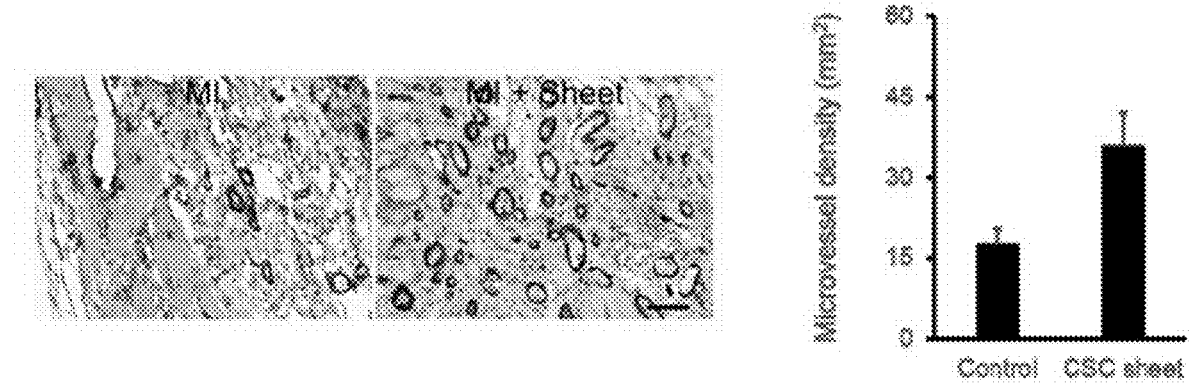
[FIG. 26]
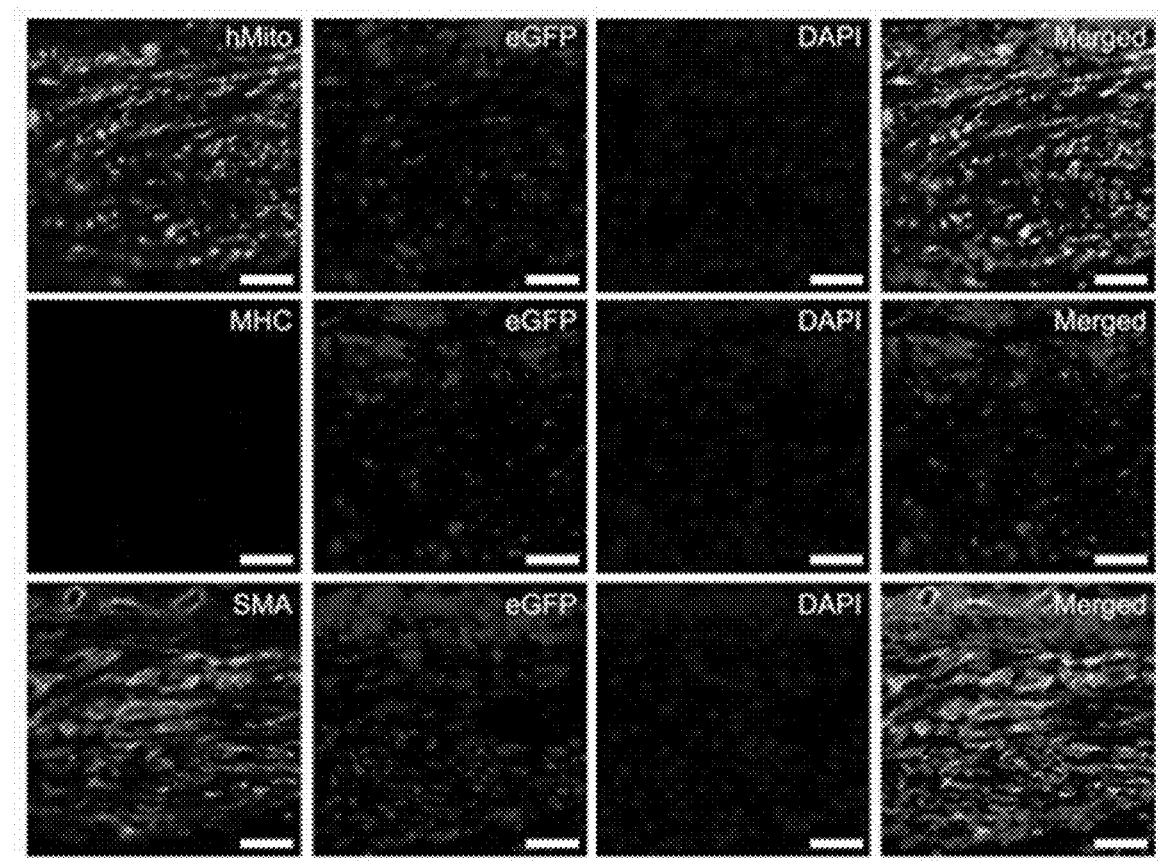

[FIG. 27]
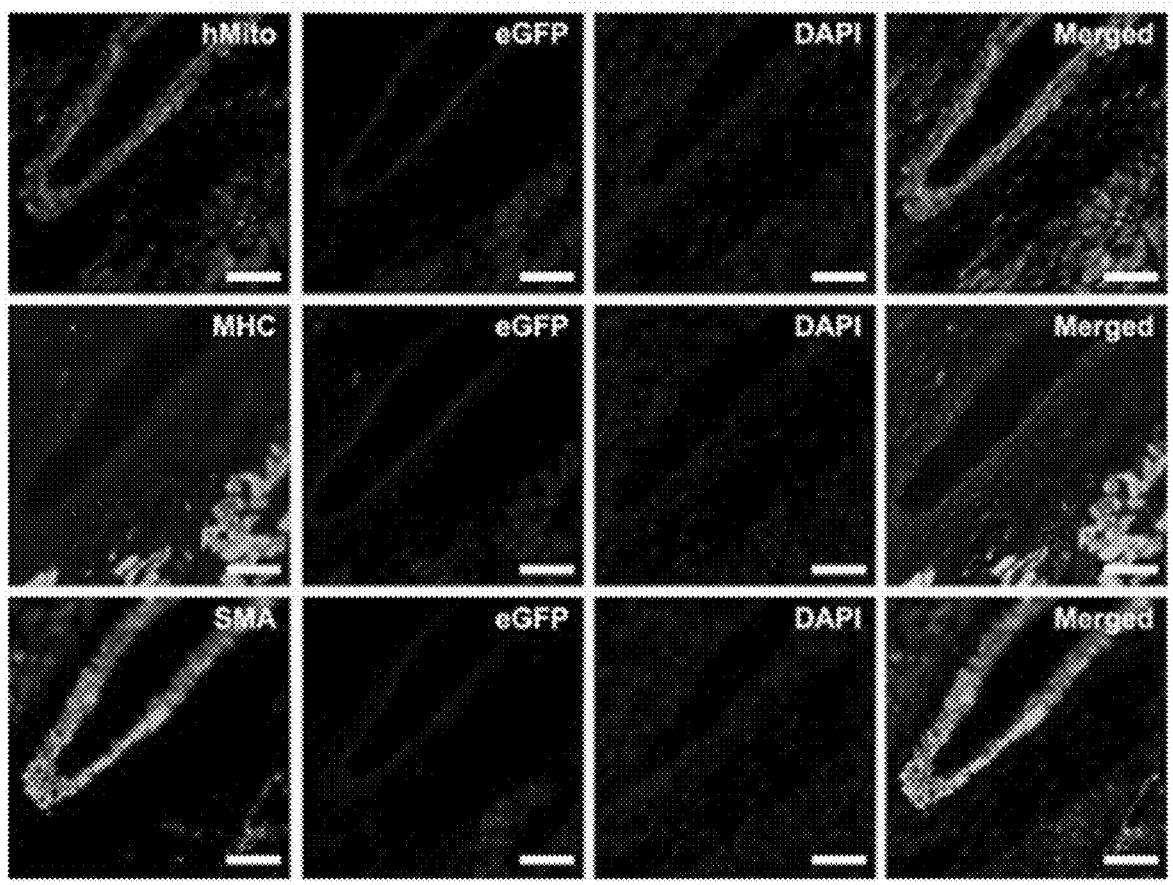

MULTILAYERED CELL SHEET OF CARDIAC STEM CELLS AND METHOD OF PREPARING THE SAME

TECHNICAL FIELD

The present disclosure relates to a multilayered cell sheet of endogenous cardiac stem cells (CSCs) derived from adult myocardial tissue and a method of preparing the multilayered cell sheet. The endogenous CSCs derived from adult myocardial tissue are embedded in a hydrogel, and then, subjected to three-dimensional culture to be assembled in multiple layers, thereby preparing a multilayered cell sheet. The multilayered cell sheet can be then applicable as a therapeutic agent for myocardial regeneration that can regenerate damaged myocardial tissue.

BACKGROUND ART

Ischaemic heart diseases or primary (idiopathic) or secondary cardiomyopathies are accompanied by congestive heart failure due to myocardial dysfunction caused by damage, death, and loss of myocardial cells. In adults, lost myocardial cells are not regenerated again so that myocardial tissue is replaced with fibroblast and scar. Since myocardial function is lost on this occasion, regeneration of myocardial cells is suggested as the only treatment. In order to regenerate such damaged myocardial tissue, treatment methods using a cell or stem cell-based therapeutic and a tissue engineering product prepared according to a stem cell therapy technology are on the rise.

A stem cell-based therapeutic transplanted into the injured heart has been suggested to induce myocardial regeneration through two mechanisms. The first mechanism suggested that the transplanted stem cells are directly differentiated into cells constituting myocardium (e.g., cardiomyocytes, vascular endothelial cells, vascular smooth muscle cells, and the like) to thereby induce myocardial regeneration. The second mechanism suggested an indirect paracrine mechanism that the stem cells induce myocardial regeneration through secretion of bioactive factors capable of inducing myocardial regeneration, the bioactive factors including anti-inflammatory cytokines/factors that alleviate inflammatory response, cytokines/factors that protect myocardial cells, cytokines/factors that can induce angiogenesis, and the like. Hematopoietic stem cells (HSCs), endothelial progenitor cells (EPCs) or mesenchymal stem cells (MSCs) derived from fat tissue may induce myocardial regeneration through the second mechanism. However, in addition to embryonic stem cells and induced pluripotent stem cells, CSCs are the only cells among adult stem cells that are recognized as adult stem cells having these two mechanisms for myocardial regeneration, unlike other stem cells. Thus, CSCs are recognized as ideal cell-based therapeutics having all the requirements as cell-based therapeutics for myocardial regeneration.

In order to maximize the clinical results of stem cell-based therapeutics, a variety of transplantation methods have been attempted to increase the transplantation efficiency. As methods currently being used for delivering and transplanting a stem cell-based therapeutic into the heart, (1) systemic administration via intravenous infusion route, (2) delivery to myocardium via transcoronary infusion route, (3) intramyocardial injection, (4) epicardial implantation, and the like have been suggested. In the case of injecting a conventional stem cell-based therapeutic into the peripheral vein or coronary artery, or performing intramyocardial injection, less than 1% of the administered cells are delivered to the heart and survive, resulting in low delivery rate to the heart, low retention rate, low engraftment rate, and the like. In order to overcome such problems above, a delivery route for transplanting a stem cell-based therapeutic into the epicardium after being seeded on a scaffold has been suggested. In this case, the cells can be protected from excessive inflammatory response and free radicals in damaged myocardium, and cell death due to anoikis phenomenon can be also minimized. The stem cell-based therapeutic that is locally transplanted into the epicardium via the scaffold is known to induce myocardial regeneration through secretion of bioactive factors.

The stem cell-based therapeutic should have high delivery efficiency into the heart, and the delivered stem cell-based therapeutic should stay in the damaged myocardium for a long period of time, and be stagnated and retained therein. In addition, the cells delivered into the heart may successfully exhibit therapeutic effects, only when being survived (engraftment) in a severely damaged site. To increase the myocardial regeneration efficacy of the cell-based therapeutic, there is a need for techniques of, first, directing the delivery rate into the myocardium; second, increasing migration and retention rates of the cells delivered to the damages site; and third, increasing an engraftment rate of the cells that are migrated to retained in the damaged myocardium. To meet these conditions, studies have been attempted to locally deliver to the epicardium through a scaffold or an implant prepared by tissue-engineering techniques. For the transplantation of the stem cell-based therapeutic into the epicardium, a technique of transplantation after being embedded in a scaffold and a method of preparing a cell sheet are currently the most widely used.

In the related art, has been most widely used as a carrier for local delivery of a stem cell-based therapeutic to the heart. Such a scaffold can provide an extracellular matrix that is essential for the cell survival and the maintenance of cell function, and in this regard, the survival rate of cells may be increased during the delivery of the cell-based therapeutic. In addition, a scaffold may be physically fixed in myocardium or epicardium, and thus has advantages of increasing delivery and retention rates in the heart. Here, a scaffold is made of a natural or synthetic polymer having biodegradability, i.e., being biodegradable in the living body, and is prepared in the form of a hydrogel and a porous sponge. A hydrogel can be easily prepared in desired shape and size as compared with a porous sponge type scaffold, and also has advantages of being able to load and deliver cells at high density. However, a hydrogel has a weak physical strength so that it is difficult to fix on the epicardium, and in this regard, a hydrogel scaffold is the most widely used for injection into the myocardium after being mixed with a stem cell-based therapeutic. Meanwhile, a porous sponge type scaffold is difficult to be prepared in various sizes and shapes, but is easy to control physical strength thereof. Thus, a porous sponge type scaffold is used as a carrier for transplantation of a stem cell-based therapeutic into the epicardium. However, a porous sponge type scaffold is difficult to deliver cells at high density, and disadvantages that it induces foreign and inflammatory responses upon a cross-linking reaction made for the purpose of improving physical properties have been suggested.

To address the problems that a scaffold has during the delivery of a stem cell-based therapeutic, a technique of producing a stem cell-based therapeutic in the form of a cell sheet for local delivery in the living body has been reported. In the related art, to prepare a multilayered cell sheet, a method of preparing a multilayered cell sheet has been proposed, the method including: preparing a single-layered cell sheet first; and stacking the prepared single-layered cell sheet in multiple layers by using a pipette, a supporting membrane, or a special manipulator. However, when preparing a cell sheet consisting of 5 layers or more, the stacking of the single-layered cell sheet causes a problem that the supply of oxygen and nutrients to the inside of the cell sheet is limited a problem that the supply of oxygen and nutrients to the inside of the cell sheet, resulting in the occurrence of cell damage. Consequently, it was found that only a multilayered cell sheet consisting of less than 5 layers had biological effectiveness. The stacking of the single-layered cell sheet can be performed by layering a three-layered cell sheet four times at intervals of five days. However, the entire time for the preparation takes at least 20 days, and the biological properties of constituent cells within the cell sheet may be possible changed. In addition, after angiogenesis is induced within a three-layered sheet transplanted in the living body, the multilayered cell sheet may obtain therapeutic effects only through repeated transplantation processes. That is, when a thick cell sheet is prepared by a technique known to date, there may be a safety problem since a lot of time and a special culture container and a manipulator are required. If each process of the preparation is not carefully manipulated, a resulting cell sheet may be damaged and more likely to have a chance of contamination during attachment and/or detachment and movement of the cell sheet, as compared with a single step culture procedure.

DESCRIPTION OF EMBODIMENTS

Technical Problem

Provided is a method of manufacturing a multilayered cell sheet according to a three-dimensional single step culture procedure by using, as a three-dimensional scaffold, a biodegradable natural polymer hydrogel and embedding cardiac stem cells (CSCs) in the hydrogel.

In addition, provided is a multilayered cell sheet of CSCs, the multilayered cell sheet including: a hydrogel in which the CSCs are embedded; and extracellular matrix (ECM), anti-inflammatory factors, protective factors for myocardial cells, cardiomyogenic factors, and proangiogenic factors, which are secreted from the CSCs.

In addition, provided is a composition for treating a heart disease, the composition including, as an active ingredient, a multilayered cell sheet of CSCs and a culture product of the multilayered cell sheet.

Solution to Problem

To achieve the above technical problems, the present disclosure provides a method of manufacturing a multilayered cell sheet of cardiac stem cells (CSCs), the method including steps of: (1) isolating and culturing CSCs; (2) embedding the cultured CSCs in a hydrogel; (3) culturing the hydrogel including the CSCs embedded therein under stressed culture conditions in which a physical support is applied to prevent cell-mediated hydrogel compactions; and (4) culturing the resulting hydrogel of step (3) under non-stressed culture conditions in which a physical support is excluded to induce cell-mediated hydrogel compaction.

In addition, the present disclosure provides a multilayered cell sheet of CSCs, the multilayered cell sheet including: a hydrogel in which the CSCs are embedded; and extracellular matrix (ECM), anti-inflammatory factors, protective factors for myocardial cells, myocardial regeneration factors, and angiogenic factors, which are synthesized and secreted from the CSCs and accumulated in the hydrogel.

In addition, the present disclosure provides a composition for treating a heart disease, the composition including, as an active ingredient, the multilayered cell sheet of the CSCs or a culture product of the multilayered cell sheet.

Advantageous Effects of Disclosure

The present disclosure relates to a multilayered cell sheet of CSCs and a method of manufacturing the same. In particular, the present disclosure provides a method of manufacturing a multilayered cell sheet according to a single step culture procedure by using, as a three-dimensional scaffold, a biodegradable natural polymer hydrogel and embedding CSCs in the hydrogel. The present disclosure is aimed to provide a novel method of manufacturing a multilayered cell sheet of CSCs, the method capable of preventing a sheet damage problem and a risk of sheet contamination, which are caused by physical vulnerability during the conventional manufacturing of the multilayered cell sheet, and shortening the manufacturing time by changing a multistep culture procedure to a single step culture procedure. Furthermore, the multilayered cell sheet of the CSCs of the present disclosure may enhance physical characteristics through cell-to-cell adhesion and cell-to-hydrogel polymer adhesion, and also enhance biological functions by accumulating bioactive factors and extracellular matrix (ECM), which are produced and secreted from the CSCs during cell culturing, in the multilayered cell sheet.

BRIEF DESCRIPTION OF DRAWINGS

FIG. 1 shows a process of isolating cardiac stem cells (CSCs) by using a three-dimensional hydrogel-supported myocardium culture method.

FIG. 2 shows two-dimensional culture of the CSCs that migrate from myocardium and outgrow in a hydrogel.

FIG. 3 shows self-renewal capacity of the CSCs.

FIG. 4 shows in vitro growth capability of the CSCs.

FIG. 5 shows immunophenotype characteristics of CSCs.

FIG. 6 shows fibrinolytic activity of the CSCs and an effect of plasminogen activator inhibitor (PAI) of controlling the fibrinolytic activity of the CSCs.

FIG. 7 shows the results of fibrinolytic activity and cytoplasmic spreading of the CSCs depending on compositions of a fibrin hydrogel and introduction of the PAI.

FIG. 8 shows effects of the PAI on cytoplasmic spreading and intercellular adhesion of the CSCs in a three-dimensional fibrin hydrogel depending on an administration method of PAI.

FIG. 9 shows the results of CSC-mediated hydrogel compactions depending on a density of the CSCs embedded in a hydrogel and introduction of the PAI.

FIG. 10 shows the results of resistance of collagen, fibrin, and GPT hydrogel against the CSC-mediated hydrogel compactions under stressed culture conditions.

FIG. 11 shows the compactions of CSCs-mediated GPT and fibrin hydrogel under non-stressed culture conditions.

FIG. 12 shows the compactions of CSCs-mediated GPT and fibrin hydrogel over the period of non-stressed culture.

FIG. 13 shows the results of cell death and caspase 3/7 activity of the CSCs in the fibrin hydrogel over the period of the non-stressed culture.

FIG. 14 shows the results of comparing CSCs outgrown according to a single step culture procedure in a hydrogel with those cultured according to a three-dimensional hydrogel-supported culture method, in terms of the expression of anti-inflammatory factors, protective factors for myocardial cells, induction factors for myocardial regeneration, and angiogenic factors.

FIG. 15 shows the results of mRNA expression of bioactive factors of the CSCs according to culture conditions (stressed culture conditions and non-stressed culture).

FIG. 16 shows condensation and water release of hydrogel fibrils in the multilayered cell sheet of the CSCs over the period of the non-stressed culture.

FIG. 17 shows cell layers stacked in the multilayered cell sheet depending on the number of CSCs that are to be embedded in the hydrogel.

FIG. 18 shows intercellular binding (beta-catenin) and cell-to-ECM binding (integrin-beta1) in the multilayered cell sheet of the CSCs.

FIG. 19 shows that intercellular adhesion (connexin 43) and accumulation of extracellular matrix (collagen type IV, laminin, fibronectin, and the like) are increased in the multilayered cell sheet of the CSCs over the period of the stressed culture.

FIG. 20 shows immunophenotype characteristics of the CSCs that constitute the multilayered cell sheet.

FIG. 0.21 shows secretion capability of angiogenic factors in the multilayered cell sheet of the CSCs.

FIG. 22 shows an engraftment rate of the multilayered cell sheet of the CSCs that are transplanted into epicardium and migration capability of the CSCs to damaged myocardium.

FIG. 23 shows ingrowth of host microvessels and engraftment of multilayered cell sheet of the CSCs that are transplanted into epicardium.

FIG. 24 shows effects of the multilayered cell sheet of the CSCs on myocardial regeneration, myocardium protection, and anti-fibrosis in a myocardial infarction model.

FIG. 25 shows effects of the multilayered cell sheet of the CSCs on enhancement of angiogenesis in a myocardial infarction mode.

FIG. 26 shows the results of differentiation characteristics of the CSCs in the multilayered cell sheet located in epicardium.

FIG. 27 shows differentiation capability of the CSCs, which migrate from the multilayered cell sheet to myocardium, into myocardial cells and vascular smooth muscle cells.

BEST MODE

Thus, the inventors of the present disclosure have attempted to improve the time and complicated process required in the manufacturing of a thick multilayered cell sheet according to a method known to date, and to prevent various limitations including laborious process, the need for specialized equipment to stack a single layered cell sheet, mechanical fragility, and contamination. The present disclosure provides a method of manufacturing a multilayered cell sheet according to a single step culture procedure by using a biodegradable natural polymer hydrogel, as a three-dimensional matrix, and embedding cardiac stem cells (CSCs) in the hydrogel. The present disclosure is aimed to provide a novel method of manufacturing a multilayered cell sheet of CSCs, the method capable of overcoming a sheet vulnerability due to physicomechanical fragility and preventing a risk of sheet contamination during the conventional manufacturing of the multilayered cell sheet by shortening the manufacturing time by changing a multi-step culture process to a single-step culture process. Furthermore, the multilayered cell sheet of CSCs of the present disclosure may enhance physicomechanical property through cell-to-cell adhesion and cell-to-hydrogel polymer adhesion, and also enhance biological functions by accumulating bioactive factors and extracellular matrix (ECM), which are produced and secreted from CSCs during cell culturing, in the multilayered cell sheet. The present disclosure has been accomplished according to a method of enhancing myocardial regeneration by increasing a delivery rate, a retention rate, and an engraftment rate of a stem cell-based therapeutics via delivery to the epicardium.

The present disclosure provides a method of manufacturing a multilayered cell sheet of cardiac stem cells (CSCs), the method including steps of: (1) isolating and culturing CSCs; (2) embedding the cultured CSCs in a hydrogel; (3) culturing the hydrogel comprising the CSCs embedded therein under a stressed culture condition in which a physical support is applied; and (4) culturing the resulting hydrogel of step (3) under a non-stressed culture condition in which a physical support is excluded.

Preferably, the CSCs may be isolated from cardiac tissue, but embodiments of the present disclosure are not limited thereto.

Preferably, in step (2), the cultured CSCs may be mixed with a hydrogel in a solution phase, and the solution phase converts to a gel phase so that the CSCs may be uniformly distributed in a three-dimensional manner in the hydrogel. Preferably, such a phase transition from the solution phase to the gel phase may be controlled in about 30 seconds to about 4 minutes.

Preferably, the hydrogel may be a natural polymer or a synthetic polymer, and examples thereof include fibrin, collagen, gelatin, chitosan, PLLA, PEG, peptide, and the like. However, embodiments of the present disclosure are not limited thereto. A polymer content in a three-dimensional hydrogel may be in a range of about 0.1% to about 5%, and preferably, may be less than about 0.5%.

More preferably, the hydrogel may be a fibrin hydrogel, and such a fibrin hydrogel may include fibrinogen at a final concentration in a range of about 0.1% to about 1%, thrombin at a final concentration in a range of about 0.2 U/ml to about 2 U/ml, and plasminogen activator inhibitor (PAI) at a final concentration in a range of about 10 µg/ml to about 500 µg/ml.

More preferably, the PAI may include tranexamic acid, aminomethylbenzoic acid, aminocaproic acid, or aprotinin, embodiments of the present disclosure are not limited thereto.

Preferably, the cultured CSCs of step (2) may be added to a thrombin solution, but embodiments of the present disclosure are not limited thereto.

Preferably, the cultured CSCs of step (2) may have a density in a range of about $1\times10^6$/ml to about $1\times10^8$/ml, but embodiments of the present disclosure are not limited thereto.

More preferably, to control the number of cell layers in the multilayered cell sheet of the CSCs, CSCs at a density in a range of about $1\times10^6$/ml to about $1\times10^8$/ml may be mixed with a hydrogel in a solution phase, and the mixed hydrogel may be transferred at a volume in a range of about 10 µl/mm² to about 500 µl/mm² to a mold having a specific shape. Through polymerization/crosslinking at a temperature of 37° C. for 2 hours, the phase of the hydrogel is changed to a gel phase, and accordingly, the CSCs may be uniformly distributed in a three-dimensional manner. More preferably, CSCs at a density in a range of about $2.5\times10^6$/ml to about $1\times10^7$/ml were mixed and transferred at a volume in a range of about 100 μl/mm² to about 300 μl/mm², thereby manufacturing a multilayered cell sheet of the CSCs. Here, by controlling the cell density and volume, a multilayered cell sheet consisting of about 10 layers to about 50 layers may be manufactured.

Preferably, the stressed culture condition of step (3) in which the physical support is applied may include casting the hydrogel including the CSCs embedded therein on a circular, rectangular, or square mold so that the CSCs are cultured under a stressed condition in which a physical support is applied.

Preferably, the stressed culture condition of step (3) may induce cell-to-cell adhesion and cell-to-hydrogel polymer adhesion. When cultured under the stressed culture condition for 1 day to 5 days, the cells embedded in the hydrogel may be adhered to fibrillary chains of the hydrogel, and may also induce cytoplasmic spreading, cell migration, and cell-to-cell adhesion, thereby improving physical characteristics of the manufactured multilayered cell sheet.

Preferably, according to the culture under the stressed culture condition of step (3), extracellular matrix (ECM), anti-inflammatory factors, protective factors for myocardial cells, myocardial regeneration factors, and angiogenic factors, which are produced and secreted from the SCSs, may be accumulated in the hydrogel.

More preferably, the ECM may include fibronectin, laminin, or collagen type IV; the anti-inflammatory factors may include interleukin (IL), such as IL-6 or IL-10, or a transforming growth factor (TGF), such as TGF-β; the protective factors for myocardial cells may include IL-6, IL-11, cardiotrophin-1, hepatocyte growth factor (HGF), insulin-like growth factor (IGF)-1, or leukemia inhibitory factor (LIF); the myocardial regeneration factors may include fibroblast growth factor (FGF), bone morphogenetic protein (BMP), or Sox-17; and the angiogenic factors may include angiopoietin based or FGF based, or comprise hepatocyte growth factor (HGF) or vascular endothelial growth factor (VEGF), but embodiments of the present disclosure are not limited thereto.

Preferably, the non-stressed culture condition (i.e. free-floating culture condition) of step (4) may induce cell-mediated hydrogel compaction so that culture media and water in the hydrogel may be extruded.

Preferably, the multilayered cell sheet of the CSCs may consist of about 10 layers to about 50 layers, but embodiments of the present disclosure are not limited thereto.

In addition, the present disclosure provides a multilayered cell sheet of CSCs, the multilayered cell sheet including: a hydrogel in which the CSCs are embedded; and ECM, anti-inflammatory factors, protective factors for myocardial cells, myocardial regeneration factors, and angiogenic factors, which are secreted from the CSCs and accumulated in the hydrogel.

Preferably, the hydrogel may be a fibrin hydrogel, and such a fibrin hydrogel may include fibrinogen at a final concentration in a range of about 0.1% to about 1%, thrombin at a final concentration in a range of about 0.2 U/ml to about 2 U/ml, and PAI at a final concentration in a range of about 10 μg/ml to about 500 μg/ml.

More preferably, the PAI may include tranexamic acid, aminomethylbenzoic acid, aminocaproic acid, or aprotinin, but embodiments of the present disclosure are not limited thereto.

In one embodiment, the hydrogel in the multilayered cell sheet of the CSCs does not induce inflammatory and foreign reactions in vivo, and may have biodegradable characteristics that the hydrogel is completely degraded in vivo within 3 days to 3 weeks.

Preferably, the CSCs may have a density in a range of about $1\times10^6$/ml to about $1\times10^8$/ml, but embodiments of the present disclosure are not limited thereto.

Preferably, the multilayered cell sheet of the CSCs may consist of about 10 layers to about 50 layers, but embodiments of the present disclosure are not limited thereto.

In the multilayered cell sheet of the CSCs of the present disclosure, a cell membrane may remain intact, and adhere on a hydrogel polymer and an ECM support, so that stable structural characteristics may be resulted. Accordingly, a survival rate of the CSCs in a hostile environments, which enrich by an inflammatory mediators and/or excessive oxygen free radicals on a damaged site, may be increased.

In addition, the present disclosure provides a composition for treating a heart disease, the composition including, as an active ingredient, the multilayered cell sheet of CSCs or a culture product of the multilayered cell sheet.

Preferably, the composition may reduce the degree of myocardium fibrosis that is induced after cardiac injury, promote angiogenesis and myocardial regeneration, and promote cardiac contraction function by increasing a thickness of myocardium.

Preferably, heart disease may include ischaemic heart disease or primary (idiopathic) or secondary cardiomyopathy, and the primary (idiopathic) cardiomyopathy may include dilated cardiomyopathy (DCM), hypertrophic cardiomyopathy (HCM), or restrictive cardiomyopathy, but embodiments of the present disclosure are not limited thereto.

In particular, the multilayered cell sheet of the CSCs of the present disclosure provides a method of stably increasing a delivery rate, a retention rate, and an engraftment rate in the heart after being delivered to the epicardium of the damaged heart, and also provides a cell therapeutic method of promoting myocardial regeneration/protection and recovering cardiac functions by delivering factors for myocardial regeneration/protection, angiogenic factors, and anti-inflammatory factors, which are secreted from the multilayered cell sheet of the CSCs, to the damaged myocardium site.

Mode of Disclosure

Hereinafter, exemplary embodiments will be described in detail to promote understanding of the present disclosure. It should be noted, however, that the following examples are illustrative examples of embodiments and are not intended to limit the scope of the present disclosure in any way. These examples are provided so that this disclosure will be thorough and complete, and will fully convey the concept of examples to those skilled in the art.

<Example 1> Isolation and Culture of Cardiac Stem Cells (CSCs) from Adult Myocardium After approval of the Institutional Review Board of College of Medicine, Inje University, isolation of CSCs from adult myocardium was attempted. The isolation of the CSCs was performed according to the method disclosed in KR 10-1389850. The myocardium was donated by a brain-dead patient, and epicardium and endocardium around the myocardium were removed. Then, the resulting myocardium was cut into fragments, each having a size of about 1 mm³, and the fragments were washed 5 times with Dulbecco's phosphate-buffered saline (DPBS) solution. Meanwhile, thrombin (Sigma-Aldrich, Seoul, Korea) was dissolved in Dulbeco's Modified Eagles Media (DMEM, Invitrogen, Seoul, Korea) to prepare 1 unit/ml thrombin solution, and human plasma-derived fibrinogen (Greencross, Seoul, Korea) to prepare 0.25% fibrinogen solution. The myocardium fragments were dispersed in the 0.25% thrombin solution, and the myocardium fragments in the 0.25% thrombin solution was added to the same amount of the 0.25% fibrinogen solution. Then, 10 mL of the mixed solution was loaded onto a 100-mm culture dish. The culture dish was put in a 37° C. incubator for 2 hours to allow a reaction for gel formation. After a fibrin hydrogel was formed, 10 ml of a cell culture medium was added thereto. Here, the cell culture medium had a composition of 90% DMEM (Welgene, Gyeongsan City, Korea), 10% fetal bovine serum (FBS, Gibco, Seoul, Korea), 10 ng/ml epidermal growth factor (EGF, Peprotech, Seoul, Korea), 2 ng/ml basic fibroblast growth factor (bFGF, Peprotech, Seoul, Korea), 10 ng/ml insulin-like growth factor (IGF, Peprotech, Seoul, Korea), and 10 µg/ml gentamicin (Invitrogen). Afterwards, the culture dish was subjected to incubation for 2 weeks with stirring on an orbital shaker at a speed of 30 rpm. A fresh cell culture medium was replaced every 2 days. The CSCs were migrated from the myocardium to the fibrin hydrogel and outgrown CSCs therein were treated with 10,000 unit urokinase (Greencross) to degrade the fibrin hydrogel, and released CSCs were collected. The collected CSCs were expanded and cultured according to conventional monolayer culture conditions. At a density of more than 80%, the cultured CSCs were recovered from the cell culture dish by using 0.05% trypsin/EDTA (Sigma-Aldrich, Seoul, Korea), and then, subcultured.

As shown in FIG. 1, by using a three-dimensional fibrin hydrogel-supported organ culture method, migration and outgrowth of cells from myocardium were able to be induced. That is, migration and outgrowth of the CSCs were able to be induced from the myocardium, and when the myocardium fragments were embedded three-dimensionally in the hydrogel, migration of the CSCs was observed within 24 hours. After 1 week of the culture, the number of cells migrating from the myocardium to the hydrogel and outgrowing in the hydrogel was increased. In addition as the culture period increased, the number of cells migrating from the myocardium and outgrowing in the hydrogel was also increased in a proportional manner.

After 2 weeks of the organ culture, the cells migrating to the hydrogel and outgrowing therein were treated with 10,000 unit urokinase, which is a fibrin-degrading enzyme, thereby degrading the fibrin hydrogel and collecting released cells. Here, 95% or more of the free cells isolated from the hydrogel were survived, and the collected CSCs were expanded and cultured according to conventional monolayer culture conditions. As shown in FIG. 2, the CSCs showed a typical spindle-shaped appearance in the monolayer culture conditions. At a density of more than 80%, the cultured CSCs were recovered from the cell plate by using 0.05% trypsin/EDTA (Sigma-Aldrich, Seoul, Korea), and then, expanded and cultured.

<Example 2> Growth Characteristics and Immunophenotype Characteristics of CSCs Derived from Adult Myocardium In vitro growth capability of CSCs derived from adult myocardium was evaluated on the basis of population doubling time (PDT). The immunophenotype of the isolated and the CSCs were analyzed by using a confocal laser scanning microscope after immunofluorescence staining was performed on the cells.

1) Self-Renewal Capability of CSCs

The self-renewal capability of the CSCs was evaluated by colony forming ability and PDTs. In order to evaluate a forming ability of colony forming unit-fibroblast (CFU-F), the CSCs expanded according to the monolayer culture method were seeded on a 100-mm culture dish at a density of 5 cells/cm$^2$, and then, a growth culture medium was added thereto. On the 7$^{th}$ day of incubation, cells in the culture dish were fixed with 2% formalin for 10 minutes, and then, subjected to staining with 0.1% crystal violet (LabChem Inc., Pittsburgh, Pa.). The forming ability of the CFU-Fs was measured by counting the number of colonies having a diameter of 2 mm or more by using an image analysis program (Image J, NIH, Bethesda, Md.). Then, the number of colonies per seeded the number of the seeded cells was calculated and expressed as a percentage (%).

As shown in FIG. 3, the CSCs formed colonies (15%) in the monolayer culture condition, and the colonies were composed of densely packed clusters of spindle cells. That is, it was confirmed that the CSCs had self-renewal capability.

2) In Vitro Growth Capability of CSCs

In vitro growth capability of the CSCs was evaluated by calculating population doubling time (PDT) in the monolayer culture conditions. One thousand cells were seeded on a 48-multiwell culture plate, and then, cultured for 3 days. The cells were lysed by using CelLytic™ MT lysis reagent (Sigma-Aldrich, Seoul, Korea), and DNA content in a sample of the lysed cells was measured by using Quant-iT™ PicoGreen reagent (Molecular probes, Eugene, Oreg.). Fluorescent microplate reader, Synergy™ HT; Bio-Tek Instruments, Neufahrn, Germany) was used to measure a fluorescent intensity at an emission wavelength of 485 nm and an excitation wavelength of 540 nm. To convert the measured fluorescence intensity into cell number, a standard curve was obtained by using the cells isolated from the myocardium, and the standard curve was used to convert the fluorescent intensity in the sample into cell population. PDT was then determined according to the following equation: PDT= [(days in exponential phase)/((log N2-log N1)/log 2)], wherein N1 is a cell population in an initial period in an exponential growth phase, and N2 is a cell population in a terminal period in the exponential growth phase.

As shown in FIG. 4, the CSCs were able to be subcultured more than 18 times in the monolayer culture conditions. Until the 18-passage subcultures, the PDT of the CSCs was in a range of about 35.7 hours to about 45.3 hours in average, showing excellent in vitro proliferation capacity. In addition, as the subculture was performed more times, the PDT was slightly increased, but cell ageing was not shown until the 18-passage subcultures. Accordingly, it was confirmed that the cells isolated from the cells derived from the myocardium had excellent self-renewal capability and growth capability.

3) Immunophenotype Characteristics of CSCs

To analyze immunophenotype characteristics of the CSCs, immunofluorescence staining was performed. Thirty thousand cells amplified and cultured in the the single step culture condition were seeded on a 4-multiwell chamber slide (Lab-Tek™ II Chamber Slide™ System, Thermo Fisher Scientific, Seoul, Korea), and then, cultured for 1 day. Afterwards, the cells were fixed with a solution of acetone/methanol mixed at 1:1. To inhibit non-specific reaction of antibody, the cells were reacted with 5% bovine serum albumin (BSA, Fraction V, IgG-free, Thermo Fisher Scientific) at room temperature for 30 minutes. Primary antibodies used for the evaluation of the immunophenotype characteristics were CSC markers, such as nestin, nkx-2.5, GATA-4, CD105, Sca-1, CD140b, and c-kit; myocardial cell markers, such as α-sarcomeric actinin and myosin heavy chain; vascular endothelial cell markers, such as CD31, CD34, CD146, and flk-1; smooth muscle cell markers, such as α-smooth muscle actin (SMA), hematopoietic cell markers, such as CD14, CD45, and CD133; and mesenchymal stem cell markers, such as CD29, CD44, CD73, and CD90. Then, signals were detected by a reaction with the corresponding primary antibody, isotype-matched Alexa Fluor 488-conjugated IgG, at room temperature for 45 minutes. Nuclei of the cells were stained by using 10 μg/ml DAPI (4',6-diamidino-2-phenylindole, Invitrogen) solution, and then, were analyzed by using a confocal microscope. As shown in FIG. 5, the CSCs that were expanded in vitro according to the single step culture procedure showed an expression rate of the CSC markers as follows: nestin (98.8%±3.7%), nxk-2.5 (93.4%±2.1%), GATA-4 (96.4%±3.2%), CD105 (98.2%±4.2%), CD140b (90.1%±2.1%), and Sca-1 (95.7%±4.1%). The CSCs showed an expression rate of at least 90% in the mesenchymal stem cell markers, such as CD29, CD44, CD73, and CD90, but an expression rate of less than about 1% in c-kit. The CSCs showed an expression rate of less than about 1% in the vascular endothelial cell markers, the smooth muscle cell markers, the myocardial cells, and the hematopoietic cell markers. According to these results, it was confirmed that the CSCs derived from the myocardium have the same immunophenotype characteristics as undifferentiated stem cells derived from the myocardium.

<Example 3> Enhancement of Structural Stability of Fibrin Hydrogel as a Three-Dimensional Matrix Based on Inhibitory Effect of PAI on Fibrinolytic Activity of CSCs To evaluate the fibrinolytic activity of the CSCs and the role of PAI which inhibits fibrinolysis, 100 μg/ml of tranexamic acid, which is one type of the PAI, was used. Human plasma-derived fibrinogen (Greencross, Seoul, Korea) was mixed with a DMEM supplemented with 10 mM $CaCl_2$ to prepare a fibrinogen solution having a final concentration of 0.25%, and thrombin (Sigma, St. Louis, Mich.) was dissolved in a DMEM to prepare a thrombin solution having a final concentration of 0.25 U/ml. One million CSCs were mixed with 1 ml of the thrombin solution to prepare a thrombin solution in which the CNCs were dispersed. Afterwards, the fibrinogen solution and the thrombin solution containing the CSCs were mixed at a ratio of 1:1, and 100 μl of the mixed solution was transferred to a 24-multiwell cell culture plate. The cell culture plate was placed in an incubator at a temperature of 37° C., and the cells and fibrinogen were allowed for polymerization and crosslinking reactions for 2 hours, thereby preparing a fibrin hydrogel. Afterwards, a DMEM supplemented with 10% calf serum (CS) and 10 μg/ml of gentamicin was added to the resulting cell culture plate. Then, the culture cell plate was placed in an orbital shaker for incubation at a speed of 15 rpm for 1 day. Here, a hydrogel not containing a PAI (hereinafter, referred to as a PAI-free hydrogel) was used as a control group.

As shown in FIG. 6, a hydrogel of the PAI-free hydrogel was completely dissolved from the first day of incubation by fibronolytic factors secreted from the CSCs, and thus, failed to provide a three-dimensional matrix that the CSCs could attach and outgrow. Here, it was also confirmed that most cells were adhered to the cell culture plate for two-dimensional growth. Meanwhile, in the case of the hydrogel containing the PAI, the structure of the hydrogel was well maintained, thereby providing a three-dimensional matrix for the CSCs. The CSCs in the hydrogen were uniformly distributed in a three-dimensional manner. From the first day of the incubation, the spreading of the cytoplasm was observed, and on the second day of the incubation, the intercellular binding was observed. According to these results, it was confirmed that, when the cells were embedded in the fibrin hydrogel and cultured, the fibrin hydrogel was dissolved depending on the fibrinolytic activity of the CSCs, resulting in losing a role as a three-dimensional matrix. Meanwhile, due to the introduction of the PAI, the fibrinolytic activity of the CSCs was inhibited, so that the fibrin hydrogel was able to serve as a three-dimensional matrix for the CSCs. In addition, in this regard, the fibrin hydrogel was able to support the cytoplasmic spreading and the intercellular adhesion.

<Example 4> Cytoplasmic Spreading of CSCs Depending on PAI Introduction and Fibrin Hydrogel Compositions To evaluate the cytoplasmic spreading of the CSCs depending on the concentration of fibrinogen constituting the fibrin hydrogel and the introduction of the PAI, a fibrinogen solution at a concentration of 2.5 mg/ml, 5.0 mg/ml, 10.0 mg/ml, and 20.0 mg/ml was prepared by mixing it with a DMEM supplemented with 10 mM $CaCl_2$, and a thrombin solution having a concentration of 0.5 U/ml was prepared in the same manner as in Example 1 using a DMEM. One million CSCs were dispersed in 1 ml of the thrombin solution. The thrombin solution containing the CSCs was mixed with each of the fibrinogen solution at four different concentrations at a ratio of 1:1, and 100 μl of the mixed solution was transferred to a 24-multiwell cell culture plate. The cell culture plate was placed in an incubator at a temperature of 37° C., and the cells and fibrinogen were allowed for polymerization and crosslinking reactions for 2 hours, thereby preparing four different fibrin hydrogels, each including 0.25 U/ml thrombin and fibrinogen at a concentration of 0.125%, 0.25%, 0.5%, and 1%. Afterwards, a DMEM supplemented with 10% CS and 100 μg/ml of gentamicin was used as a cell culture medium. Then, the culture cell plate was placed in an orbital shaker for incubation at a speed of 15 rpm for 1 day. The cytoplasmic spreading of the cells was photographed by a microscope, and the length of the cytoplasmic spreading was measured by using Image J program. Then, 200/ml of tranexamic acid, which is one type of the PAI, was added to the thrombin solution, so as to evaluate whether the introduction of the PAI affected the cytoplasmic spreading.

As shown in FIG. 7, in the same manner as in Example 1, a hydrogel of the PAI-free fibrin hydrogel was completely dissolved from the first day of incubation so that the cells filed to have three-dimensional distribution and were rather adhered to the bottom of the cell culture plate. That is, PAI-free fibrin hydrogel has lost its role as a three-dimensional matrix by fibronolytic factors secreted from the CSCs. Meanwhile, the in the case of the fibrin hydrogel containing the PAI, the structure of the fibrin hydrogel as well maintained, thereby providing a three-dimensional matrix for the CSCs. However, it was confirmed that the CSCs in the fibrin hydrogel containing fibrinogen at a high concentration showed reduced cytoplasmic spreading in a proportional manner to the fibrinogen concentration. According to these results, it was confirmed that the introduction of the PAI had little effect on the cytoplasmic spreading, but the concentration of fibrinogen was considered as a significant inhibitor of the cytoplasmic spreading.

<Example 5> Effect of PAI on Cytoplasmic Spreading of CSCs and Intercellular Adhesion in Three-Dimensional Fibrin Hydrogel Evaluation to confirm whether, depending on the introduction of the PAI, the PAI affected the cytoplasmic spreading of the CSCs and the intercellular adhesion in the hydrogel was attempted. In the same manner as in Example 1, a fibrin hydrogel consisting of 0.125% fibrinogen and 0.25 U/ml thrombin was prepared, and the CSCs and the PAI were added thereto. Here, a DMEM supplemented with 10% CS and 100 μg/ml of gentamicin was used as a cell culture medium. During the incubation, a PAI-free fibrin hydrogel (−/−) was used as a control group. After incubation for 6 hours and 12 hours, the resulting cells were fixed with 1% formalin for 1 hours, and then, put in 1% albumin/PBS for a reaction with 0.2 unit/pi of Oregon Green™ 488-conjugated phalloidin for 30 minutes. After a washing process using PBS was performed thereon, the resulting cells were stained with 10 μg/ml of DAPI for 5 minutes, and then, were analyzed by using a confocal microscope.

As shown in FIG. 8, the cytoplasmic spreading was limitedly observed in the hydrogel (−/−) without any PAI and the hydrogel without PAI in the cell culture medium. Meanwhile, the hydrogel (+/+) with PAI introduced in the cell culture medium during the manufacturing process of the hydrogel served as a three-dimensional matrix that the cells could attach. In addition, active cytoplasmic spreading and intercellular adhesion were observed in the CSCs included in the hydrogel (+/+). Accordingly, it was confirmed that the PAI introduced to a hydrogel or the like continuously acts as an important factor for three-dimensional growth and adhesion of the cells during incubation in the fibrin hydrogel.

<Example 6> Effect of PAI on Adhesion to Fibrin Hydrogel, Cytoplasmic Spreading, Intercellular Adhesion, and Hydrogel Compactions The PAI was evaluated for the effect on cell-mediated hydrogel compactions by adding 200 μg/ml tranexamic acid to a thrombin solution. 0.25% fibrinogen was mixed with 0.5 U/ml thrombin containing, per milliliter (ml), $1\times10^6$, $2\times10^6$, and $1\times10^7$ CSCs, respectively, at a ratio of 1:1, and 100 μl of the mixed solution was cast on a 5-mm O-ring. The O-ring was placed in an incubator at a temperature of 37° C., and the cells and fibrinogen were allowed for polymerization and crosslinking reactions for 1 hour. Then, 1 ml of a DMEM supplemented with 1% CS was added thereto. Afterwards, the O-ring was placed in an orbital shaker for incubation at a speed of 15 rpm for 12 hours for dynamic incubation. The cells were cultured for 24 hours while being attached to the O-ring, and were detached from the O-ring. Then, in a non-stressed culture condition, the resulting cells were cultured for 2 hours. Afterwards, the compaction rate of the hydrogel was analyzed, and the cytoplasmic spreading and intercellular adhesion of the cells were evaluated in a microscopic view.

As shown in FIG. 9, the active cytoplasmic spreading and intercellular adhesion were observed in the PAI-containing fibrin hydrogel, whereas the cytoplasmic spreading and the intercellular adhesion were not observed in the PAI-free fibrin hydrogel. The microscopic observations also revealed that the hydrogel around the CSCs had hollows upon fibrinolysis, and thus, due to the loss of polymer fibrils to which the cells could attach, the cytoplasmic spreading and the intercellular adhesion of the cells were not observed. Meanwhile, the addition of the PAI led to the active cell attachment and diffusion, and the intercellular binding was increased as the incubation period was longer. The PAI-free hydrogel showed no hydrogel compactions even in a non-stressed culture condition, whereas the PAI-containing hydrogel showed cell-mediated hydrogel compactions depending on the cell concentration. According to these results, it was confirmed that the CSC-mediated hydrogel compactions occurred only in the presence of the cytoplasmic spreading and the intercellular adhesion, and that the PAI played an important role in the cell attachment and the intercellular adhesion.

<Example 7> Resistance to CSC-Mediated Compactions by Hydrogel Type

To evaluate resistance of the hydrogel to CSC-mediated compactions in the stressed culture conditions, CSCs at a density of $5\times10^5$/ml, $1\times10^6$/ml, $2\times10^6$/ml, and $5\times10^6$/ml were embedded in a 0.2% collagen hydrogel, a 0.125% fibrin hydrogel containing 100 μg/ml of tranexamic acid, and a 3% GTP hydrogel, respectively. Then, each hydrogel was transferred to a 24-multiwell cell culture plate, and the cells were cultured for 1 day. Here, a growth culture medium was the same as the one used in Example 1. After 1 day of the incubation, the cells were fixed with formalin, and stained with toluidine blue. Then, changes in the hydrogel structure were evaluated in terms of cell status.

As shown in FIG. 10, a hydrogel of the collagen hydrogel including the CSCs at a low density was spontaneously detached from the cell culture plate upon cell-mediated compaction, a hydrogel of the collagen hydrogel including the CSCs at a high concentration was also detached from the cell culture plate upon the cell-mediated compactions. Meanwhile, a hydrogen of each of the fibrin hydrogel and the GPT hydrogel was resistant to the cell-mediated compactions, thereby confirming the such a hydrogel had a three-dimensional structure. That is, depending on components and types of hydrogel, physicomechanical properties vary, resulting in different resistance to the cell-mediated compactions. In particular, it was confirmed that, due to weak physicomechanical property of the collagen hydrogel, hydrogel compactions could occur as breaking form a frame even in low-concentration cells.

<Example 8> CSC Attachment, Cytoplasmic Spreading, Intercellular Adhesion, and Cell-Mediated Hydrogel Compactions According to the Type of Hydrogel In the present Example, a hydrogel consisting of 0.2% fibrinogen, 0.25 U/ml thrombin, and 100 μg/ml tranexamic acid and 3% GPT hydrogels each containing 2.8 kPa of elastic modulus 5.1 kPa of elastic modulus. $5\times10^6$/ml of CSCs were embedded in each of these hydrogels, attached to an O-ring for 1 day for incubation (in a stress condition). Then, the cells were detached from the O-ring, and cultured again for 2 hours in the non-stressed culture conditions. Each of the hydrogels was then fixed with formalin to prepare paraffin blocks and sections. Hematoxylin-eosin staining was performed thereon, thereby evaluating the attachment of the CSCs to the hydrogel, and the cytoplasmic spreading and the intercellular adhesion of the CSCs in the hydrogel.

As shown in FIG. 11, the 3% GPT hydrogels (2.8 kPa and 5.1 kPa) showed reduced intercellular adhesion and had the CSC-mediated hydrogel compaction rate of less than about 10%. Meanwhile, the fibrin hydrogel showed active cytoplasmic spreading and intercellular adhesion of the CSCs, resulting in 50% or more of hydrogel compactions. Consequently, it was confirmed that, depending on the physicomechanical properties of the hydrogel and the cell-to-hydrogel adhesion, the cytoplasmic spreading and the intercellular adhesion of the CSCs were significantly affected, and accordingly, the CSC-mediated compactions were also significantly affected.

<Example 9> CSC-Mediated Compactions of Fibrin Hydrogel and Cell Death According to Culture Conditions To evaluate the CSC-mediated compactions and cell retention of the fibrin hydrogel in a stressed culture condition and a non-stressed culture condition, a 0.125% fibrinogen solution was mixed with a 0.5 U/ml thrombin solution containing 200 μg/ml of tranexamic acid and $1×10^7$/ml of CSCs, at a ratio of 1:1, 100 μl of the mixed solution was transferred to a 5-mm O-ring. The O-ring was placed in an incubator at a temperature of 37° C., and the cells and fibrinogen were allowed for polymerization and crosslinking reactions for 2 hours. A DMEM supplemented with 10% CS and 100 μg/ml of gentamicin was used as a cell culture medium, and added to the O-ring. Then, the cells were cultured for 3 days in the stressed culture conditions while being attached to the O-ring. After the cells were detached from the O-ring, the resulting cells were cultured for 30 minutes, 2 hours, and 3 days, separately, in the non-stressed culture conditions. The CSCs-mediated hydrogel compactions dependent upon the culture conditions were analyzed by using Image J program. The hydrogel was fixed with formalin to prepare paraffin blocks and sections, Hematoxylin-eosin staining was performed thereon, thereby evaluating the injury and death of the CSCs in the hydrogel. To quantitatively evaluate the cell injury and death, the activity of caspase 3/7 in the hydrogel including the CSCs embedded therein was analyzed by using Apo 3/7 HTS™ assay kit (Cell Technology, Minneapolis, Minn.). After being treated with PBS containing 1% Tween20 for 10 minutes, 100 μl of a sample in which the cells were dissolved was reacted with an equal amount of caspase 3/7 detection reagent at a temperature of 37° C. for 30 minutes, and the resultant was analyzed by measuring fluorescence intensity thereof using a fluorescent microplate reader (fluorescent microplate reader, SpectraMax M2, Molecular Devices) at an emission wavelength of 488 nm and an excitation wavelength of 530 nm.

As shown in FIG. 12, it was confirmed that, the CSCs-mediated hydrogel compactions were significantly increased with increasing incubation time in the non-stressed culture conditions. As shown in FIG. 13, the longer the incubation time in the non-stressed culture conditions, the more the cytoplasmic damage and nuclear fragmentation frequently were increased. Accordingly, the CSCs-mediated hydrogel compactions were increased with increasing incubation time in the non-stressed culture conditions. Consequently, it was confirmed that the supply of nutrients and oxygen into the hydrogel was prohibited, resulting in the occurrence of cell injury and death. Furthermore, with increasing incubation time in the non-stressed culture conditions, the activity of caspase 3/7 is also increased in a proportional manner to the incubation time. Accordingly, it was confirmed that the non-stressed culture conditions could lead to excessive cell-mediated hydrogel compactions, resulting in increasing cell injury and death.

<Example 10> Expression of Bioactive Genes in Fibrin Hydrogel According to Culture Conditions In the same manner as in Example 9, $5×10^6$/ml of CSCs were embedded in a hydrogel containing 100 μg/ml of tranexamic acid, 0.125% fibrinogen, and 0.25 U/ml thrombin. 100 μl of the mixed solution was transferred to a 5-mm O-ring, and the O-ring was placed in an incubator at a temperature of 37° C., and the cells and fibrinogen were allowed for polymerization and crosslinking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring or in the non-stressed culture conditions. Here, the CSCs expanded and cultured according to a monolayer culture method were used as a control group. After 3 days of incubation, RNA was isolated from the CSCs cultured in the hydrogel or on the culture plate, and subjected to reverse transcription to generate cDNA, Here, the mRNA expression of the anti-inflammation factors (e.g., IL-6, IL-10, and TGF-b), the myocardial cell protection factors (e.g., IL-6, IL-11, CT-1, HGF, IGF-1, and LIF), the cardiogenic factors (e.g., FGF-2, FGF-7, FGF-9, BMP-2, BMP-4, and Sox-17), the proangiogenic factors (e.g., Ang-1, Ang-2, bFGF, HIF-1α, HGF, or VEGF), and the myocardial cell inducible factors (e.g., BMP-4 or sox-17) was evaluated via real time-quantitative PCR.

As shown in FIG. 14, it was confirmed that the three-dimensionally cultured CSCs in the hydrogel showed significantly increased mRNA expression of the anti-inflammation factors, the myocardial cell protection factors, the cardiogenic factors, and proangiogenic factors, as compared with the CSCs cultured according to the monolayer culture conditions. As shown in FIG. 15, it was confirmed that the hydrogel of the CSCs cultured in the stressed culture conditions had significantly increased mRNA expression of proangiogenic mRNAs, such as angiopoietin (Ang)-1, Ang-2. fibroblast growth factor (bFGF), hepatocyte growth factor (HGF), vascular endothelial growth factor (VEGF), hypoxia inducible factor-1a, bone morphogenetic rrotein4 (BMP4), which can induce differentiation into cardiomyocytes, and Sox17, as compared with the hydrogel of the CSCs cultured in the non-stressed culture conditions. That is, it was confirmed that the CSCs included in the hydrogel and cultured in the stressed culture conditions could increase the production of bioactive factors that can induce angiogenesis and differentiation/regeneration of myocardial cells.

<Example 11> Fibrin Condensation in the Multilayered Cell Sheet of CSCs by Cell-Mediated Compactions In the same manner as in Example 9, $5×10^6$/ml of CSCs were embedded in a hydrogel solution containing 100 μg/ml of tranexamic acid, 0.125% fibrinogen, and 0.25 U/ml thrombin. 100 μl of the mixed solution was transferred to a 5-mm O-ring, and the O-ring was placed in an incubator at a temperature of 37° C. The cells and fibrinogen were then allowed for polymerization and crosslinking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 30 minutes and 2 hours in the non-stressed culture conditions to induce cell-mediated hydrogel compactions. The hydrogel was then fixed using a formalin solution to prepare paraffin blocks. Hematoxylin-eosin staining was performed thereon, and anti-fibrinogen antibodies were used to perform immunofluorescent staining thereon.

As shown in FIG. 16, it was confirmed that, as the incubation time in the non-stressed conditions increased to 30 minutes and 2 hours, the hydrogel structure was densely compact upon the CSCs-mediated compactions, water of the hydrogel polymer was extruded, fibrin fibers were condensed thick, thereby providing the multilayered cell sheet in which the CSCs were densely compacted, resulting in increased physicomechanical property.

<Example 12> Control of Cell Layer of the Multilayered Cell Sheet of CSCs by Controlling Cell Density in Hydrogel In the same manner as in Example 9, $1\times10^6$/ml, $2\times10^6$/ml, and $5\times10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and crosslinking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 2 hours in the non-stressed culture conditions to induce cell-mediated hydrogel compactions. The hydrogel was then fixed using a formalin solution to prepare paraffin blocks and sections. Hematoxylin-eosin staining was performed thereon, thereby counting the number of cell layer.

As shown in FIG. 17, it was observed that the multilayered cell sheet of the CSCs prepared by culturing the cells in the stressed culture conditions for 3 days and subsequently in the non-stressed culture conditions for 2 hours showed increase in opacity and thickness in a proportional manner to the density of the CSCs seeded on the hydrogel. In addition, according to the microscopic analysis, multilayered cell sheet prepared with a density of $1\times10^6$/ml consist of less than 10 cell layers, whereas the multilayered cell sheet prepared with a density of $5\times10^6$/ml consist of 30 cell layers or more. Accordingly, it was confirmed that the multilayered cell sheet could be manufactured into various cell layers by controlling the density of the cells to be seeded in the hydrogel.

<Example 13> Enhancement of Structural Stability Via Cell to Cell Adhesion and Cell-to-ECM Adhesion in the Multilayered Cell Sheet of CSCs In the same manner as in Example 9, $5\times10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and crosslinking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 2 hours in the non-stressed culture conditions to induce cell-mediated hydrogel compactions. The hydrogel was then fixed using a formalin solution to prepare paraffin blocks and sections. Hematoxylin-eosin staining was performed thereon, thereby evaluating intercellular adhesion. In addition, to evaluate cell-to-cell and cell-to-ECM adhesion was assessed by immunofluorescent staining with anti-β-catenin and anti-integrin-β1, respectively. In addition, the nuclei of the cells were stained with 10 μg/ml DAPI solution. Afterwards, the intercellular adhesion and the cell-to-ECM adhesion were evaluated through fluorescence microscopy.

As shown in FIG. 18, it was confirmed that anti-β-catenin involved in the intercellular adhesion was strongly expressed along with the cytoplasm, and that the intercellular adhesion was well established therein. In addition, as a result of confirming the expression of integrin-β1, which induces the binding with ECM, around the cytoplasm, it was confirmed that the cell-to-ECM adhesion could also enhance the structural properties.

<Example 14> Enhancement of Structural Stability Via Production and Accumulation of ECM in the Multilayered Cell Sheet of CSCs In the same manner as in Example 9, $5\times10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and crosslinking reactions for 2 hours. A DMEM supplemented with 10% CS and 100 μg/ml of gentamicin was used as a cell culture medium, and added to the O-ring. Then, the cells were cultured for 1 day, 2 days, and 3 days in the stressed culture conditions where the cells were attached to the O-ring. Afterwards the hydrogel was detached from the O-ring, and then, cultured again for 2 hours in the non-stressed culture conditions to induce cell-mediated hydrogel compactions. The hydrogel was then fixed using a formalin solution to prepare paraffin blocks and sections. Hematoxylin-eosin staining was performed thereon, thereby evaluating production and accumulation of ECM. To inhibit non-specific reaction, the cells were treated with 5% goat serum for 30 minutes, and then, blocked. Then, primary antibodies, such as anti-connexin 43, anti-collagen type IV, anti-laminin, and anti-fibronectin, were used for a reaction at a temperature of 37° C. for 1 hour. A washing process using PBS was performed thereon three times, and a secondary antibody, such as isotype-matched Alexa Fluor 488-conjugated antibody, was used for a reaction at room temperature for 30 minutes. The nuclei of the cells were stained with 10 μg/ml DAPI solution. After being mounted with ProLong-Gold antifade reagent (Molecular Probe), a confocal microscope was used to evaluate whether newly synthesized ECM was deposited or not.

As shown in FIG. 19, it was confirmed that basal lamina-like ECM in the multilayered cell sheet of the CSCs was accumulated in the hydrogel, wherein such ECM was produced in the cells through in vitro culture. The ECM accumulated through in vitro culture was increased in proportion to the period of the stressed culture conditions. According to these results, it was confirmed that the multilayered cell sheet of the CSCs was able to enhance the structural stability thereof by ECM that are produced by the cells, secreted therefrom, and accumulated in the multilayered cell sheet.

<Example 15> Immunophenotype of CSCs in the Multilayered Cell Sheet

In the same manner as in Example 9, $5 \times 10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and cross-linking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 2 hours in the non-stressed culture conditions to induce cell-mediated hydrogel compactions and accordingly prepare a multilayered cell sheet. Then, double immunofluorescence staining was performed by using paraffin sections to assess the immunophenotype of the cells constituting the multilayered cell sheet. Here, the paraffin sections were reacted with anti-nestin, followed by with isotype-matched Alexa Fluor 594-conjugated secondary antibody. Then, after a reaction with anti-cardiac troponin I and anti-myosin heavy chain, a reaction with isotype-matched Alexa Fluor 488-conjugated secondary antibody was made to perform double immunofluorescence staining. Here, the nuclei of the cells were stained with DAPI (Invitrogen) for fluorescence microscopy.

As shown in FIG. 20, the CSCs constituting the multilayered cell sheet showed strong expression of nestin, which is a CSC marker, whereas showed no expression of cardiac troponin I (cTnI) or myosin heavy chain (MHC), which are cardiomyocyte cell markers. That is, it was confirmed that cells constituting a cell sheet constituted a multilayered cell sheet composed of undifferentiated CSCs.

<Example 16> Secretion Capability of Proangiogenic Factors by the Multilayered Cell Sheet of CSCs In the same manner as in Example 9, $5 \times 10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and cross-linking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 2 hours in the non-stressed culture conditions to induce cell-mediated hydrogel compactions and accordingly prepare a multilayered cell sheet. To evaluate secretion capability of proangiogenic factors by multilayered cell sheet of the CSCs, the multilayered cell sheet of the CSCs was cultured in a DMEM supplemented with 1% CS for 1 day or 3 days. The cell culture medium was collected, and the concentration of proangiogenic factors in the collected cell culture medium was evaluated by enzyme-linked immunosorbent assay (ELISA). Here, proangiogenic factors secreted from CSCs in the monolayer culture conditions were used as a control group. The secretory level of the proangiogenic factors, such as Ang-1, Ang-2, bFGF, HGF, and VEGF was analyzed by using ELISA kit (R&D Systems, Minneapolis, Minn.).

As shown in FIG. 21, the multilayered cell sheet of the CSCs showed significantly improved secretion capability of the proangiogenic factors, as compared with the CSCs cultured in the monolayer culture conditions. In addition, it was confirmed that the multilayered cell sheet of the CSCs was able to continuously secrete the angiogenic factors for 3 days.

<Example 17> Transplantation of the Multilayered Cell Sheet of CSCs to Epicardium, Engraftment of the Multilayered Cell Sheet of CSCs, and Migration of the Multilayered Cell Sheet of CSCs to Damaged Site In the same manner as in Example 9, $5 \times 10^6$/ml of CSCs were embedded in 1 ml of a hydrogel solution containing 100 μg/ml tranexamic acid, 0.125% fibrinogen, and 0.25 U/ml thrombi. The, 100 μl of the mixed solution was transferred to a 5-mm O-ring, and the O-ring was placed in an incubator at a temperature of 37° C. The cells and fibrinogen were then allowed for polymerization and cross-linking reactions for 2 hours. A DMEM supplemented with 10% CS and 100 μg/ml of gentamicin was used as a cell culture medium, and added to the O-ring. Then, the cells were cultured for 3 days in the stressed culture conditions where the cells were attached to the O-ring. Afterwards, the hydrogel was detached from the O-ring, and then, cultured again for 2 hours in the non-stressed culture conditions to induce cell-mediated hydrogel compactions and accordingly prepare a multilayered cell sheet. To evaluate cell viability and migration ability, CSCs labeled with 10 μM CM-Dil were used to prepare a multilayered cell sheet. The prepared multilayered cell sheet of the CSCs was then preserved with PBS, and within a day, was transplanted into a rat model of acute myocardial infarction. As a model with acute myocardial infarction for animal experiments, Sprague Dawley rat weighing between 240 g and 260 g and being maintained in the general housing conditions was used after approval of the Ethics Commission of College of Medicine, Inje University. The myocardial infarction was induced by blocking vascular circulation via ligation of the left anterior descending coronary artery. After 30 minutes of the arterial ligation, the multilayered cell sheet of the CSCs was engrafted on the epicardium around the myocardial infarction site, wherein the multilayered cell sheet was securely fixed by making four sutures (right and left and top and bottom). After 3 days, 1 week, and 2 weeks of the transplantation of the multilayered cell sheet of the CSCs, the heart was extracted and fixed with formalin to prepare paraffin blocks and sections. Then, the cell viability and migration of the transplanted cells were evaluated As shown in FIG. 22, the cell sheet was tightly attached along with the epicardium. The cells constituting the multilayered cell sheet were found to have preserved their cytoplasmic and nuclear architecture, confirming that the CSCs were viable. The CSCs labeled with CM-Dil (in red) were distributed extensively along with the outer wall of the heart after 1 week of the transplantation, but the number of the CM-Dil positive CSCs was decreased after 2 weeks of the transplantation. However, the CM-Dil positive CSCs were migrated into the damaged myocardium from the epicardium of the heart, and accordingly, it was confirmed that the transplantation into the epicardium enabled for the CSCs to be stably implanted to the epicardium and other damaged sites.

As shown in FIG. 23, on the third day of the transplantation of the multilayered cell sheet of the CSCs, blood vessels containing blood cells were found in the multilayered cell sheet, indicating that the transplanted multilayered cell sheet of the CSCs could survive through the blood circulation between the implants and recipient host animals.

<Example 18> Protective Ability of the Multilayered Cell Sheet of CSCs

A multilayered cell sheet of CSCs was prepared in the same manner as in Example 17, and then, transplanted into the epicardium of the heart of the model where myocardial infarction was induced. To evaluate the effects of the transplanted multilayered cell sheet of the CSCs on the heart protection and the myocardial regeneration, on the $4^{th}$ week of the transplantation of the multilayered cell sheet, the heart was extracted and fixed with formalin to prepare paraffin blocks and sections. The paraffin sections were subjected to hematoxylin-eosin staining and Masson's trichrome staining, thereby analyzing myocardium damages and myocardium fibrosis. The thickness of the left ventricle wall was calculated by using Image J program, and the area of fibrosis myocardium was measured by histomorphometry.

As shown in FIG. 24, following preparing an animal model with myocardial infarction, the rat model was transplanted with the multilayered cell sheet of the CSCs and had a significantly increased thickness of the left ventricle, as compared with that in a control rat model that was not transplanted with the multilayered cell sheet. In addition, the rat model also showed significant reduction in fibrosis lesion in the infarcted left ventricle. According to these results, it was suggested that the transplantation of the multilayered cell sheet of the CSCs was effective in significantly reducing myocardial loss and fibrosis associated with myocardial infarction.

<Example 19> Proangiogenic Ability of the Multilayered Cell Sheet of CSCs

To evaluate proangiogenesis ability of a multilayered cell sheet of CSCs transplanted in vivo into myocardium, a multilayered cell sheet of CSCs was prepared in the same manner as in Example 17, and then, transplanted into the epicardium of the heart of the model with acute myocardial infarction. On the $4^{th}$ week of the transplantation of the multilayered cell sheet, the heart was extracted and fixed with formalin to prepare paraffin blocks and sections. To evaluate vessel density in myocardial infarction, anti-smooth muscle actinin (SMA) antibodies were used to perform immunohistochemical staining. Here, the microvessel density per unit area was calculated by using Image J program.

As shown in FIG. 25, the microvessel density in the damaged myocardium after myocardial infarction was significantly increased in a group where the multilayered cell sheet of the CSCs was transplanted (represented by CSC sheet), as compared with that in a group where the multilayered cell sheet was not transplanted (represented by Control). According to these results, it was suggested that the multilayered cell sheet of the CSCs was effective in promoting the myocardial protection and regeneration by promoting the myocardial regeneration and the angiogenesis in the model with acute myocardial infarction.

<Example 20> In Vivo Differentiation Characteristics and Roles of CSCs in the Multilayered Cell Sheet To investigate in vivo differentiation characteristics and regeneration ability of a multilayered cell sheet of CSCs, a multilayered cell sheet of CSCs was prepared in the same manner as in Example 17. Then, myocardial infarction was induced via ligation of the left anterior descending coronary artery of Sprague Dawley rat. After 30 minutes of the arterial ligation, the multilayered cell sheet of the CSCs was engrafted on any site of the epicardium. To investigate in vivo differentiation characteristics the CSCs and roles of the CSCs, lentivirus including eGFP transgene was infected to the CSCs before preparing the multilayered cell sheet. After 2 weeks of the transplantation of the multilayered cell sheet of the CSCs on the epicardium of the model with acute myocardial infarction, the heart was extracted and fixed with formalin to prepare paraffin blocks and sections. The paraffin sections were subjected to double immunofluorescence staining using eGFP or human mitochondria-specific makers (hMito) and cardiac cell-specific markers, and then, the in vivo differentiation of the cells was analyzed by using a confocal microscope. Here, anti-myosin heavy chain (MHC) was used as a myocardial cell marker, and anti-smooth muscle actin (SMA) was used as a vascular smooth muscle cell marker. In addition, Alexa Fluor-488-conjugated antibody was used.

As shown in FIG. 26, the CSCs located on the epicardium showed strong expression of eGFP proteins that were injected into the cells when preparing the multilayered cell sheet. At the same time, the expression of hMito proteins revealed that the cells survived along the outer wall of the heart. Although MHC was not expressed in the eGFP-positive CSCs located on the outer wall of the heart at the same time as the expression of the eGFP proteins and the hMito proteins, the simultaneous expression of SMA was confirmed by the differentiation of the cells into fibroblasts. The characteristic that SMA and eGFP were expressed around the vascular structure could be confirmed by the results that the injected CSCs were differentiated into vascular smooth muscle cells of the outer wall of the heart and involved in angiogenesis.

As shown in FIG. 27, the CSCs positive to eGFP and hMlto located on the myocardium showed the shape of a vascular wall and a cardiomyocyte, and these cells were formed as cardiomyocytes where eGFP and MHC were expressed at the same time and as vascular smooth muscle cells where eGFP and SMA were expressed at the same time, thereby confirming that the CSCs were involved in the myocardial regeneration and the vascular regeneration.

While particular embodiments have been particularly and described with reference to exemplary embodiments thereof, it will be understood by those of ordinary skill in the art that various changes in form and details may be made therein without departing from the spirit and scope of embodiments as defined by the following claims.

The invention claimed is:

1. A method of manufacturing a cell sheet having layered cardiac stem cells (CSCs), consisting of:
   (1) isolating and culturing CSCs;
   (2) embedding the cultured CSCs in a fibrin hydrogel, wherein the cultured CSCs, before the embedding step, have a density in a range of $2\times10^6$/ml to $5\times10^6$/ml, wherein the fibrin hydrogel comprises
      fibrinogen at a final concentration in a range of about 0.1% to about 1%,
      thrombin at a final concentration in a range of about 0.2 U/ml to about 2 U/ml, and
      plasminogen activator inhibitor (PAI) having tranexamic acid at a final concentration in a range of about 10 µg/ml to about 500 µg/ml,
      wherein step (2) comprises mixing the cultured CSCs with the fibrin hydrogel in a solution phase;
   (3) casting the fibrin hydrogel comprising the CSCs embedded therein on a physical support so that the CSCs are cultured for 1 to 5 days under culture conditions in which the physical support is applied, wherein, during the culturing of the CSCs, the solution phase of the fibrin hydrogel is converted to a gel phase so that the CSCs are uniformly distributed in a three-dimensional manner in the fibrin hydrogel,
   wherein during the culturing under the culture conditions in which the physical support is applied, extracellular matrix (ECM), anti-inflammatory factors, protective factors of myocardial cells, cardiomyogenic factors, and proangiogenic factors are secreted from the CSCs and accumulated in the fibrin hydrogel,
   wherein the physical support is selected from the group consisting of a circular, rectangular, and square mold, wherein a volume of the fibrin hydrogel being cast to the mold ranges 100 µl/mm² to about 300 µl/mm²;
   (4) removing the physical support and culturing the resulting fibrin hydrogel of step (3) under free-floating culture conditions for 30 minutes to 2 hours, wherein the free-floating culture conditions of step (4) induce cell-mediated fibrin hydrogel compaction so that water and culture media in the fibrin hydrogel are extruded; and
   (5) obtaining the cell sheet having layered CSCs.

2. The method of claim 1, wherein the CSCs are isolated from cardiac tissue.

3. The method of claim 1, wherein the culture conditions of step (3) induce cell-to-cell adhesion and cell-to-hydrogel polymer adhesion.

4. The method of claim 1, wherein the ECM comprises fibronectin, laminin, and collagen type IV.

5. The method of claim 1, wherein the anti-inflammatory factors comprise interleukin (IL) comprising IL-6 or IL-10, or transforming growth factor-β (TGF-β).

6. The method of claim 1, wherein the protective factors for myocardial cells comprises IL-6, IL-11, cardiotrophin-1, hepatocyte growth factor (HGF), insulin-like growth factor (IGF)-1, or leukemia inhibitory factor (LIF).

7. The method of claim 1, wherein the cardiomyogenic factors comprise fibroblast growth factor (FGF), bone morphogenetic protein (BMP), or Sox-17.

8. The method of claim 1, wherein the proangiogenic factors are angiopoietin or FGF, or comprise hepatocyte growth factor (HGF) or vascular endothelial growth factor (VEGF).

\* \* \* \* \*